US010111431B2

(12) United States Patent
Wang et al.

(10) Patent No.: US 10,111,431 B2
(45) Date of Patent: Oct. 30, 2018

(54) APPLICATION OF BIOFILM FORMATION INHIBITING COMPOUNDS ENHANCES CONTROL OF CITRUS CANKER

(71) Applicant: University of Florida Research Foundation, Inc., Gainesville, FL (US)

(72) Inventors: Nian Wang, Auburndale, FL (US); Jinyun Li, Winter Haven, FL (US)

(73) Assignee: University of Florida Research Foundation, Inc., Gainesville, FL (US)

(*) Notice: Subject to any disclaimer, the term of this patent is extended or adjusted under 35 U.S.C. 154(b) by 0 days.

(21) Appl. No.: 14/774,255

(22) PCT Filed: Mar. 11, 2014

(86) PCT No.: PCT/US2014/023238
§ 371 (c)(1),
(2) Date: Sep. 10, 2015

(87) PCT Pub. No.: WO2014/164694
PCT Pub. Date: Oct. 9, 2014

(65) Prior Publication Data

US 2016/0021882 A1 Jan. 28, 2016

Related U.S. Application Data

(60) Provisional application No. 61/775,975, filed on Mar. 11, 2013.

(51) Int. Cl.
*A01N 43/38* (2006.01)
*A01N 37/44* (2006.01)
*A01N 59/20* (2006.01)

(52) U.S. Cl.
CPC ............. *A01N 43/38* (2013.01); *A01N 37/44* (2013.01); *A01N 59/20* (2013.01)

(58) Field of Classification Search
None
See application file for complete search history.

(56) References Cited

U.S. PATENT DOCUMENTS

| | | | | |
|---|---|---|---|---|
| 7,163,709 B2 * | 1/2007 | Cook | A01N 59/16 | 426/321 |
| 8,529,964 B1 * | 9/2013 | Mann | A01N 59/20 | 424/630 |
| 2009/0143230 A1 | 6/2009 | Melander et al. | | |

FOREIGN PATENT DOCUMENTS

| | | | |
|---|---|---|---|
| WO | 2012030986 A2 | 3/2012 | |
| WO | 2012129621 A1 | 10/2012 | |
| WO | WO 2012129621 A1 * | 10/2012 | A01N 37/44 |

OTHER PUBLICATIONS

Lee (Lee, J-H., et al., 3-Indolylacetonitrile Decreases *Escherichia coli* O157:H7 Biofilm Formation and Pseudomonas aeruginosa Virulence, Environmental Microbiology (2011) 13(1), 62-73).*
Kolodkin-Gal (Kolodkin-Gal, I., et al., D-Amino Acids Trigger Biofilm Disassembly, Science vol. 328 Apr. 30, 2010 pp. 627-629).*
Rigano (Rigano, L.A., et al., Biofilm Formation, Epiphytic Fitness, and Canker Development in Xanthomonas axonopodis pv. citri., MPMI vol. 20, No. 10, 2007, pp. 1222-1230. doi:10.1094/MPMI-20-10-122).*
Graham, J.H., et al., "Xanthomonas axonopodis pv. citri: factors affecting successful eradication of citrus canker", Molecular Plant Pathology, 2004, vol. 5, pp. 1-15.*
Canker-literature, Florida Department of Agriculture (accessed Jun. 12, 2018, at https://www.freshfromflorida.com/content/download/11484/145200/canker-literature.pdf).*
Kolodkin-Gal et al., "D-amino acids trigger biofilm disassembly", Science, Apr. 2010, vol. 328, No. 5978, pp. 627-629.
Lee et al., "3-Indolylacetonitrile decreases *Escherichia coli* 0157:H7 biofilm formation and Pseudomonas aeruginosa virulence", Environmental Microbiology, 2011. vol. 13, No. 1, pp. 62-73.
Shiotani, H. et al, "Survival and disperxal of Xanthomonas citri pv. citri from infected Satsuma mandarin fruit", Crop Protection, 2009, vol. 28, pp. 19-23.
Guo, Yinping et al., "Requirement of the galU Gene for Polysaccharide Production by and Pathogenicity and Growth in Planta of *Xanthomonas citri* subsp. *citri*", Applied and Environmental Microbiology, Apr. 2010, vol. 76, No. 7, pp. 2234-2242.
Teixeira E.C. et al., "The copper resistance operon copAB from Xanthomonas axonopodis pathovar citri: gene inactivation results in copper sensitivity", Microbiology, 2008, vol. 154, pp. 402-412.
Gottwald, T. et al., "The epidemiological significance of post-packinghouse survival of *Xanthomonas citri* subsp. *citri* for dissemination of Asiatic citrus canker via infected fruit", Crop Protection, 2009, vol. 28, pp. 508-524.

(Continued)

*Primary Examiner* — H. Sarah Park
(74) *Attorney, Agent, or Firm* — Timothy H. Van Dyke; Beusse, Wolter, Sanks & Maire PLLC

(57) ABSTRACT

*Citrus* canker caused by the bacterium *Xanthomonas citri* subsp. *citri* (Xac) is an economically important disease of *citrus* worldwide. Biofilm formation plays an important role in early infection of Xac on host leaves. In this study, we assessed the hypothesis that small molecules able to inhibit biofilm formation reduce Xac infection and enhance the control of *citrus* canker disease. D-leucine and 3-indolylacetonitrile (IAN) were found to prevent biofilm formation by Xac on different abiotic surfaces and host leaves at a concentration lower than the minimum inhibitory concentration (MIC). Quantitative real¬time reverse transcription polymerase chain reaction (qRT-PCR) analysis indicated that IAN repressed expression of chemotaxis/motility-related genes in Xac. In laboratory experiments, planktonic and biofilm cells of Xac treated with D-leucine and IAN, either alone or in combination, were more susceptible to copper (CuSO4) than those untreated. In greenhouse assays, D-leucine and IAN applied alone, or combined with copper reduced both the number of canker lesions and bacterial populations of Xac on *citrus* host leaves. This study provides the basis for the use of foliar-applied biofilm inhibitors for the control of *citrus* canker alone or combined with copper-based bactericides.

13 Claims, 8 Drawing Sheets

(56) References Cited

OTHER PUBLICATIONS

Hasman, Henrik et al., "The effect of pH and storage on copper speciation and bacterial growth in complex growth media", Journal of Microbiological Methods, 2009, vol. 78, pp. 20-24.
Teitzel, Gail M. et al., "Heavy Metal Resistance of Biofilm and Planktonic Pseudomonas aeruginosa", Applied and Environmental Microbiology, Apr. 2003, vol. 69, No. 4, pp. 2313-2320.
Yan, Qing et al., "High-Throughput Screening and Analysis of Genes of *Xanthomonas citri* subsp. *citri* Involved in Citrus Canker Symptom Development", MPMI, 2012, vol. 25, No. 1, pp. 69-84.
Hochbaum, Allon I. et al., "Inhibitory Effects of D'Amino Acids on *Staphylococcus aureus* Biofilm Development", Journal of Bacteriology, Oct. 2011, vol. 193, No. 20, pp. 5616-5622.
Laia, Marcelo L. et al., "New genes of *Xanthomonas citri* subsp. *citri* involved in pathogenesis and adaptation revealed by a transposon-based mutant library", BMC Microbiology, 2009, vol. 9, issue 12, 17 pages.
Li, Jinyun et al., "Genome-Wide Mutagenesis of Xanthomonas axonopodis pv. citri Reveals Novel Genetic Determinants and Regulation Mechanisms of Biofilm Formation", PLOS One, Jul. 2011, vol. 6, issue 7, e21804, 16 pages.
Schaad, Norman W. et al., "Emended classification of xanthomonad pathogens on citrus", Systematic and Applied Microbiology, 2006, vol. 29, pp. 690-695.
Behlau, Franklin et al, "Copper resistance genes from different xanthomonads and citrus epiphytic bacteria confer resistance to *Xanthomonas citri* subsp. *citri*", 2012, Eur J Plant Pathology, vol. 133, pp. 949-963.
Da Silva, A.C.R. et al., "Comparison of the genomes of two Xanthomonas pathogens with differing host specificities", Nature 2002, 15 pages.
Gottig, N et al., "A Filamentous Hemagglutinin-Like Protein of Xanthomonas axonopodis pv. citri, the Phytopathogen Responsible for Citrus Canker, Is Involved in Bacterial Virulence", PLOS One, 2009, vol. 4, issue 2, e4538.
Behlau, F. et al., "Effect of frequency of copper applications on control of citrus canker and the yield of young bearing sweet orange trees", Crop Protection, 2010, vol. 29, pp. 300-305.
Brunings, A.M. et al., "Xanthomonas citri: breaking the surface", Molecular Plant Pathology, 2003, vol. 4(3), pp. 141-157.
Rigano, Luciano A. et al., "Biofilm Formation, Epiphytic Fitness, and Canker Development in Xanthomonas axonopodis pv. citri", 2007, MPMI, vol. 20, No. 10, pp. 1222-1230.
Alva, A.K., "Copper Contamination of Sandy Soils and Effects on Young Hamlin Orange Trees", 1993, Bull. Environ. Contam. Toxicology, vol. 51, pp. 857-864.
Irey, M et al., "Post-hurricane Analysis of Citrus Canker Spread and Progress towards the Development of a Predictive Model to Estimate Disease Spread Due to Catastrophic Weather Events", 2006, Plant Health Progress, 16 pages.
Gottwald, T. R. et al., Citrus Canker: The Pathogen and Its Impact, Plant Health Progress, 2002, 34 pages.
Behlau, F. et al., "Copper resistance genes from different xanthomonads and citrus epiphytic bacteria confer resistance to *Xanthomonas citri* subsp. *citri*", Eur J Plan Pathology, 2012, vol. 133, pp. 949-963.
Rodrigues, C.M., et al., "Copper resistance of biofilm cells of the plant pathogen *Xylella fastidiosa*", Appl Microbiol Biotechnology, 2008, vol. 77, pp. 1145-1157.
Hsiao, Yi-Min, "Functional Characterization of copA Gene Encoding Multicopper Oxidase in Xanthomonas campestris pv. campestris", J. Agric. Food Chemistry, 2011, vol. 59, pp. 9290-9302.
Li, Jinyun et al., "The gpsX gene encoding a glycosyltransferase is important for polysaccharide production and required for full virulence in *Xanthomonas citri* subsp. *citri*", BMC Microgiology, 2012., vol. 12, No. 31, 16 pages.
Graham, J.H. et al., "Xanthomonas axonopodis pv. citri: factors affecting successful eradication of citrus canker", Molecular Plant Pathology, 2004, vol. 5, o. 1, pp. 1-15.

* cited by examiner

APPLICATION OF BIOFILM FORMATION INHIBITING COMPOUNDS ENHANCES CONTROL OF CITRUS CANKER

CROSS-REFERENCE TO RELATED APPLICATIONS

This application is related to U.S. Provisional Application No. 61/775,975 filed Mar. 11, 2013 to which priority is claimed under 35 USC 119. The teachings of this provisional are incorporated herein in their entirety by this reference.

BACKGROUND

*Citrus* canker, caused by the Gram-negative bacterial pathogen *Xanthomonas citri* subsp. *citri* (Xac) (syn. *Xanthomonas citri, X. campestris* pv. *citri* and *X. axonopodis* pv. *citri*) (Schaad et al., 2006), is one of the major constraints to *citrus* production worldwide (Gottwald et al., 2002). *Citrus* canker affects most commercial *citrus* varieties and is widely distributed in many tropical and subtropical *citrus* growing regions (Gottwald et al., 2002, Graham et al., 2004). The disease characterizes itself as raised necrotic lesions surrounded by oily, water-soaked margins and yellow chlorotic rings on leaves, stems and fruit of infected trees; and when conditions are highly favorable for disease, it also causes defoliation, twig dieback, general tree decline, blemished fruit and premature fruit drop (Gottwald et al., 2002, Graham et al., 2004). Wind-blown rain, which facilitates invasion via stomata or wounds (Graham et al., 2004), is the primary short distance (i.e., within the same tree or between neighboring trees) spread mechanism for *citrus* canker (Gottwald et al., 2009). Severe meteorological events such as hurricanes and tornados can disseminate the disease over longer distances (key et al., 2006; Gottwald and key, 2007). However, long-distance dissemination more often occurs with the transportation of diseased propagating materials, e.g. budwood, rootstock seedlings, or budded trees, and infected fruit (Gottwald et al., 2009). Direct canker-related losses are attributed to the decrease of fruit quality and yield. Moreover, a serious consequence is the significant impact on commerce resulting from restrictions to national and international fruit trade from canker affected areas (Gottwald et al., 2002; Shiotani et al., 2009).

Copper-based bactericides are currently the primary control measure for *citrus* canker worldwide, as limited strategies exist for suppression of *citrus* canker on susceptible cultivars once the pathogen has been established (Graham et al., 2004). For effective disease control, multiple applications of copper-based bactericides are needed throughout the year due to their partial effectiveness under windblown rain conditions (Behlau et al., 2010b; Graham et al., 2010). As a consequence, long-term use of copper bactericides led to induced resistance to copper in xanthomonad populations (Ritchie and Dittapongpitch, 1991; Behlau et al., 2012) and the accumulation of copper metal in soils or ground water affecting the environment and plant health (Alva et al., 1993). Thus, there exists a need to develop novel strategies to deal with this situation. A potential approach is to develop compounds that reduce bacterial resistance to copper bactericides and, thereby enhancing the bactericidal effect and reducing the application of copper.

Much effort has been made to understand the biology and molecular basis of Xac pathogenesis over the past decade (da Silva et al., 2002; Brunings and Gabriel 2003; Laia et al, 2009; Yan and Wang, 2012). The canker bacterium, considered to be a hemibiotrophic pathogen, initially grows epiphytically (on leaf surfaces) and then enters into the host through stomata or wounds to colonize the mesophyll parenchyma and multiply in the apoplast (intercellular spaces). Xac, like many other plant pathogenic bacteria, has evolved multiple virulence factors to promote infection and establish themselves successfully in host plants (Laia et al, 2009; Yan and Wang, 2012). Among the virulence factors important for Xac infection, biofilms have been suggested to play an important role in the early stages of infection by enhancing epiphytic persistence on host leaves. Importantly, multiple mutants of Xac impaired in biofilm formation consistently exhibit a decrease in bacterial growth in planta and have reduced ability to elicit canker symptoms in susceptible *citrus* leaves (Gottig et al., 2009; Guo et al., 2010; Rigano et al., 2007; Li and Wang, 2011; Yan and Wang, 2011).

SUMMARY

The disclosure is based on the discovery that compounds that are able to inhibit biofilm formation by Xac may reduce its infection and enhance the control of canker disease. The present disclosure is based on studies investigating the activity against Xac biofilm formation of two sets of compounds, D-amino acids and indole derivatives, which have been shown to inhibit biofilm formation and influence virulence in human bacterial pathogens such as *Escherichia coli O*157:H7, *Pseudomonas aeruginosa* and *Staphylococcus aureus* (Kolodkin-Gal et al., 2010; Lee et al., 2011). It was found that D-leucine and 3-indolylacetonitrile (IAN) are active in inhibiting biofilm formation by Xac in NB liquid medium at a concentration lower than the minimum inhibitory concentration (MIC). Moreover, it was found that D-leucine and IAN increased the sensitivity of Xac to copper and reduced symptom development and bacterial populations on *citrus* leaves in greenhouse. These results provided the basis for the use of foliar-applied biofilm inhibitors for the control of microbes, either alone or combined with metal-based bactericides.

DEFINITIONS

Figure 1A:
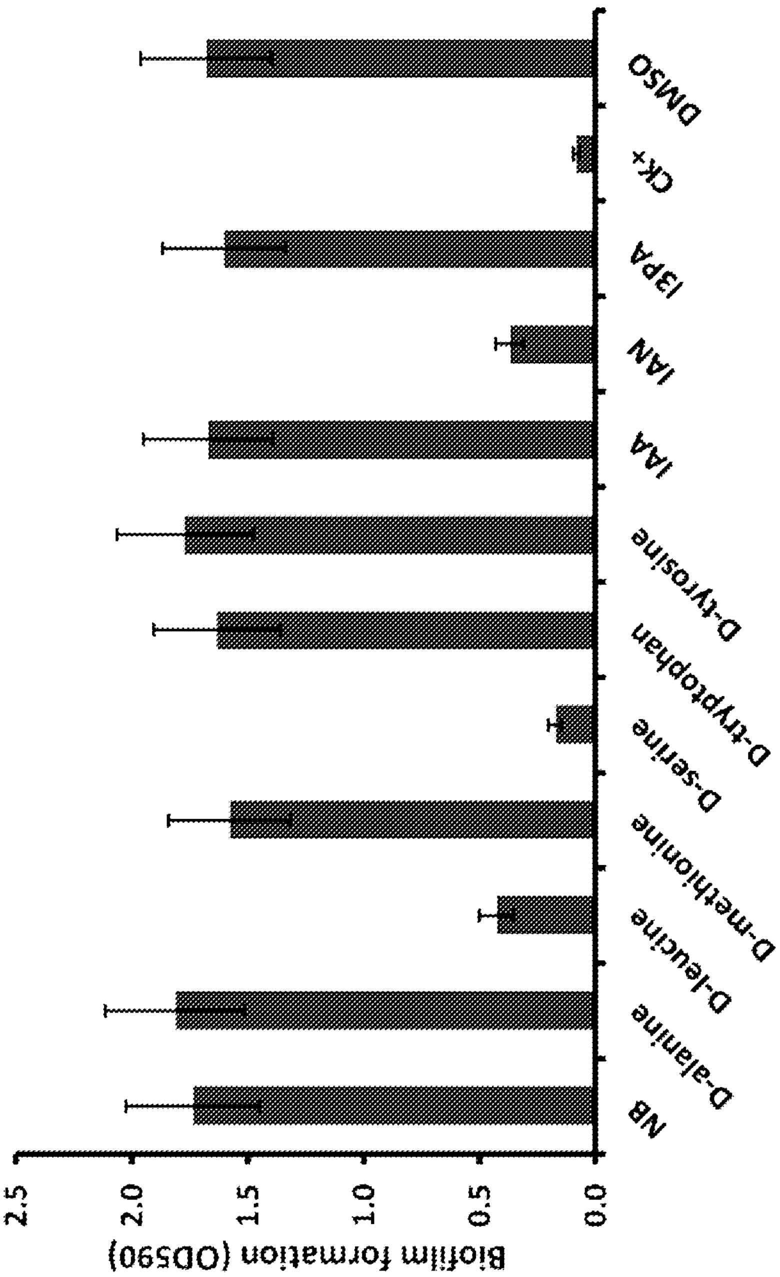
FIG. 1A-FIG. 1C A. Effect of D-amino acids at 10 mM and indole derivatives [3-indoleacetic acid (IAA), 3-indolylacetonitrile (IAN) and indole-3-propioninc acid (I3PA)] at 100 μg/mL on biofilm formation of *X. citri* subsp. *citri* strain 306 in NB medium at 28° C. after 48 h in 96-well plates. All of the indole derivatives were dissolved in 0.1% DMSO. DMSO and NB were used as the negative controls (normal biofilm formation) and no bacterial inoculation (CK+) was used as the positive control (no biofilm formation), respectively. B. Dose-dependent effect of D-leucine and D-serine (0, 5, 10, 15, 20 mM) and C. IAN (0, 25, 50, 100 and 150 μg/mL) on *X. citri* subsp. *citri* strain 306 biofilm formation. The experiments were repeated three times with similar results with eight replicates (8 wells), and the error bars indicated standard deviations.

As used herein, the term "microorganism" refers to any noncellular or unicellular (including colonial) organism. Microorganisms include all prokaryotes. Microorganisms include bacteria (including cyanobacteria), lichens, fungi, protozoa, virinos, viroids, viruses, phages, and some algae. As used herein, the term "microbe" is synonymous with microorganism.

As used herein, the term "biofilm reducing agent" refers to one of D-amino acids (D-alanine, D-leucine, D-methionine, D-serine, D-tryptophan, and/or D-tyrosine) or derivatives thereof. In addition, biofilm reducing agent refers to indole derivatives including but not limited to 3-indoleacetic acid (IAA), indole butyric acid (IBB), indole-3-lactic acid (ILA), indole-3-pyruvic acid (IPyA), indole-3-acetaldehyde (IAAld), 3-indolylacetonitrile (IAN), indole-3-propioninc acid (I3PA), and 3-methylindole. In a specific embodiment, the biofilm reducing agent is D-leucine or D-serine, or derivatives thereof, see e.g. derivatives found in Appendix A. In another specific embodiment, the biofilm reducing agent is 3-indolylacetonitrile (IAN).

As used herein, the term "metal antimicrobial agent" includes but is not limited to copper or copper containing compounds (e.g. copper sulfate). Alternatively, metal antimicrobial agents may include silver or silver containing compounds, iron or iron-containing compounds, aluminum or aluminum-containing compounds, zinc or zinc-containing compounds.

"Copper containing compounds" refer to those compounds which possess toxicity to fungi and bacteria by virtue of releasing copper (e.g. unchelated $Cu^{+2}$). The free copper penetrates into the bacterial and/or fungal microorganism in order to exert its toxic effect. Suitable copper compounds include fixed coppers [$Cu(OH)_2$], Bordeaux mixture, as well as other well known fixed copper compositions including those disclosed in CRC Handbook of Pest Management in Agriculture, Vol. 3, David Pimentel (Editor), CRC Press, Boca Raton, Fla. (1981), which is incorporated herein by reference. However, the specific copper based compound is not critical and any copper based compound which releases free copper so as to be toxic to fungi and bacteria can be used.

There are a variety of commercially available fixed copper materials with trade names such as Kocide 2000 and Kocide 3000 (E.I. Dupont Nemours), Copper Count-N (available from Mineral Research & Development Corp., Charlotte, N.C.); Champ (New Farm, Limited), CuproFix (United Phosphorus, Limited), Magna-Bon CS 2005 Magna Bon Agricultural Control Solutions, NorDox 75 WG (Nordox, Ag), MasterCop (ADAMA Agricultural Solutions, Limited) as well as soluble forms of copper (copper oleate, for example). The fixed copper, copper hydroxide for example, is the preferred form that is used in most agricultural situations because it adheres to plant parts and there is a continuous release of the free copper ion.

In one embodiment, copper containing compounds pertain to a copper salt. The term "copper salt" includes copper (I), (II) and (III) salts. Preferably the copper salt in a formulation according to the invention is a copper (I) (cuprous) or copper (II) (cupric) salt, more preferably a copper (II) salt. It may be selected for instance from copper carboxylates, copper halides, copper sulphadiazine, copper sulphate, copper sulphate pentahydrate, copper nitrate, copper carbonate, copper oxide, copper oxychloride, copper hydroxide, copper peptides, copper amino acid salts (eg, copper glutamate, copper aspartate and copper glycinate), copper silicates, copper salts of quinolines—especially hydroxyquinolines—and their derivatives (eg, the copper salt of 8-hydroxyquinoline), copper pyrithione and other copper salts of pyridine thiols, and mixtures thereof.

In one particular embodiment, the copper salt is a salt of a pyridine thiol, which may for example be a 2-pyridine thiol, 3-pyridine thiol or 4-pyridine thiol, in particular a 2- or 4-pyridine thiol. Such a pyridine thiol may be present in the form of a salt or other derivative, for instance a pyridine thiol oxide or hydroxide. A pyrithione may be present in the form of a pyrithione derivative, eg, a molecular and/or ionic complex containing the pyrithione group, such as for example a pyrithione salt or a dimer, oligomer or polymer containing a pyrithione or pyrithione salt monomer (for example, dipyrithione, also known as di-2-pyridinedisulphide-1,1'-dioxide).

Generally speaking the copper salt may be either organic or inorganic.

Suitable copper carboxylates include lactate, citrate, ascorbate, acetate, gluconate, au rate, myristate, palmitate, salicylate, aspirinate, stearate, succinate, tartrate, undecylenate, neodecanoate, carbonate and ricinoleate.

Suitable halides include copper chloride, copper bromide and copper iodide, preferably the cupric halide ($CuHal_2$) in each case.

Most typical copper salts for use in the methods and compositions described herein may include, for example, copper sulphate (in particular the pentahydrate), copper aspirinate, copper salicylate, copper pyrithione, copper silicate, the copper salt of 8-hydroxyquinoline, copper gluconate, copper chloride, copper hydroxide and copper acetate, again preferably in the form of the copper (II) salt in each case.

Other examples of copper containing compounds include, but are not limited to, copper hydroxide, copper oxychloride, tribasic copper sulfate, and elemental copper. Table 3 found on Appendix A sets forth a non-exhaustive list of copper containing compounds that would be included for the purposes described herein.

In a specific embodiment, copper containing compounds include a copper salicylate having the following molecular formula (I): $C_7H_4O_3Cu.(H_2O)_n$ (D wherein n represents 0, 1, 2 or 3; B) copper hydroxide $Cu(OH)_2$ (II); C) a copper salt having the following formula (III) $3Cu(OH)_2$—$X(Y)_n$, (III) wherein: X represents cupric ion $Cu^{2+}$ or calcium ion $Ca^{2+}$; Y means chloride ion $Cl^-$ or sulphate ion $SO_4^{2-}$; m is an integer equal to 1 or 2.

"Silver containing compounds" refer to those compounds which possess toxicity to fungi and bacteria by virtue of releasing silver. The free silver penetrates into the bacterial and/or fungal microorganism in order to exert its toxic effect. Examples of silver containing compounds includes, but is not limited to, silver halide (chlorine, bromine, or iodine), divalent silver complexes, silver salt (e.g. silver nitrate), silver zeolite, silver nanoparticles, silver phosphate, or silver fluoroborate.

As used herein, the term "microbe" refers to any plant pathogen that infects a plant and/or results in disease of a plant. In an exemplary embodiment, microbe refers to a bacterial plant pathogen.

As used herein, the phrase "canker microbe" refers to any microbe that causes a disorder of a plant, vegetable, or fruit known as a canker. Canker microbes include those of the family *Xanthomonas*. The canker microbe can be a plant canker microbe, a produce canker microbe, a tomato canker microbe, a *citrus* canker microbe, or the like. Suitable microbes of the family *Xanthomonas* include *X. axonopodis* (syns. *X campestris, X citri*), such as *Xanthomonas axonopodis* pv *citri, campestris* pv *campestris, X. campestris* pv *oryzae, X. campestris* pv *vesicatoria, X. axonopodis* pv *aurantifolia, X. anonopdois* pv *citrumelo*, and *X. aibilineans*, and the like.

As used herein, the phrase "*citrus* canker microbe" refers to any microbe that causes a disorder of *citrus* plants or fruit known as *citrus* canker. *Citrus* canker microbes include those of the family *Xanthomonas. Citrus* canker microbes from the family *Xanthomonas* include *Xanthomonas citri* subsp. *citri* (Xac) (syn. *Xanthomonas citri, X. campestris* pv. *citri* and *X. axonopodis* pv. *citri*), *X. axonopodis* pv *aurantifolia*, and the like.

As used herein, the phrase "tomato canker microbe" refers to any microbe that causes a disorder of tomato plants or fruit known as tomato canker, tomato spot, or tomato speck. Tomato canker microbes include those of the family *Xanthomonas*. Tomato canker microbes from the family *Xanthomonas* include *X. campestris* pv *vesicatoria*, and the like. Additional tomato canker microbes include *Pseudomonas syringae* pv tomato and *Clavibacter michiganensis* pv *michiganensis*.

As used herein, equipment used with *citrus* fruit and plants includes equipment used in cultivating, harvesting, storing, transporting, and processing *citrus*, such as tool, implement, container for collecting and transporting harvested fruit, transport vehicle, or the like. Such equipment includes truck, goat, bus, trailer, box, crate, cargo cover (e.g., tarp), bin, basket, ladder, power tool, hand tool, picking sack, clipper, clothing (e.g., hat, shoe, or glove), or the like.

As used herein, the term "produce" refers to food products such as fruits and vegetables and plants or plant-derived materials that are typically sold uncooked and, often, unpackaged, and that can sometimes be eaten raw.

As used herein, the phrase "plant product" includes any plant substance or plant-derived substance that might benefit from treatment with an antimicrobial agent or composition. Plant products include fruit, seeds, nuts, nut meats, cut flowers, individual plants or crops grown or stored in a field or greenhouse, house plants, and the like. Plant products include many animal feeds.

As used herein, the term "object" refers to a something material that can be perceived by the senses, directly and/or indirectly. Objects include a surface, and may include, but are not limited to, produce, plant product, or inanimate objects including a hard surface (such as glass, ceramics, metal, natural and synthetic rock, wood, and polymeric), an elastomer or plastic, woven and non-woven substrates, a *citrus* processing surface, and the like. In a specific embodiment, objects include a plant product (and its surfaces) such as trees present in a field or greenhouse, including fruit or leaves thereon. In alternative embodiment, object includes a body or stream of water or a gas (e.g., an air stream) employed in *citrus* production or processing.

Examples of crop plants that would be particularly benefited by the compositions and methods described herein include, but are not limited to, *citrus*, pomes, stone fruit, berries, fruiting vegetables, leafy vegetables, vines, root crops, fiber crops, cereal grains, or oil crops.

Examples of diseases associated with crops/uses that may be treated, ameliorated, or prevented by the method and compositions embodiments disclosed herein, include the following:

1. *Citrus*—*Xanthomonas citri* pv. *citri*/canker *citrus*
2. Pome—*Erwinia amylovora*/fire blight apple & pear 3. Stone—*Xanthomonas* arboricola/bacterial spot peach & nectarine; *Pseudomonas syringae* pv. *syringae*/blossom blast-canker cherry
4. Berries—*Xanthomonas fragariae*/angular leaf spot strawberry; *Xylella fastidiosa/leaf scorch blueberry*
5. Fruiting Vegetables—*Xanthomonas campestris* pv. *vesicatoria*/bacterial spot tomato & pepper
6. Leafy vegetables—*Pseudomonas syringae* pv. *spinaciae*/bacterial leaf spot spinach
7. Vines—*Xanthomonas campestris*/bacterial spot grape, *Xylella fastidiosa*/pierce's disease grape
8. Root Crops—*Pseudomonas solanacearum*/bacterial wilt potato
9. Fiber Crops—*Xanthomonas malvacearum*/angular leaf spot cotton
10. Cereal Grains—*Clavibacter michiganensis* pv. *nebraskensis*/goss's wilt corn
11. Oil Crops—*Xanthomonas campestris* pv. *glycines*/ bacterial pustule soybean
12. Food Safety—*Camplyobacter, Clostridium perfringens, Escherichia coli, Listeria, Salmonella*

As used herein, weight percent (wt-%), percent by weight, % by weight, and the like are synonyms that refer to the concentration of a substance as the weight of that substance divided by the weight of the composition and multiplied by 100. Unless otherwise specified, the quantity of an ingredient refers to the quantity of active ingredient.

As used herein, the term "about" modifying the quantity of an ingredient in the compositions of the invention or employed in the methods of the invention refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term about also encompasses amounts that differ due to different equilibrium conditions for a composition resulting from a particular initial mixture. Whether or not modified by the term "about", the claims include equivalents to the quantities. In a specific embodiment, the term "about" refers to an amount that is 5, 7, or 10 percent greater or lesser than the specified amount.

As used herein, the term "solvent" relates to an agriculturally safe solvent useful in an agricultural setting. Examples of a solvent used in formulation include, but not limited, water, alcohols (e.g. methanol, ethanol, 1-propanol, 2-propanol, ethylene glycol, etc.), ketones (e.g. acetone, methyl ethyl ketone, etc.), ethers (e.g. dioxane, tetrahydrofuran, ethylene glycol monomethyl ether, diethylene glycol monomethyl ether, propylene glycol monomethyl ether, etc.), aliphatic hydrocarbons (e.g. hexane, octane, cyclohexane, coal oil, fuel oil, machine oil, etc.), aromatic hydrocarbons (e.g. benzene, toluene, xylene, solvent naphtha, methylnaphthalene, etc.), halogenated hydrocarbons (e.g. dichloromethane, chloroform, carbon tetrachloride, etc.), acid amides (e.g. dimethylformamide, dimethylacetamide, N-methylpyrrolidone, etc.), esters (e.g. ethyl acetate, butyl acetate, fatty acid glycerin ester, etc.), and nitriles (e.g. acetonitrile, propionitrile, etc.). Alternatively, two or more types of such liquid solvents can be mixed at an appropriate ratio and can be then used.

In addition, current solvents used in the agricultural chemical industry and which may be used in compositions described herein include, but are not limited to, Aromatic 100, Aromatic 150, and Aromatic 200 fluid products, available from ExxonMobil Chemical Company. Aromatic 100 fluid comprises a mixture of components with some of the principle components comprising alkylbenzenes having 9 to 10 carbon atoms, the alkyl groups primarily being methyl and ethyl groups, and some of the principle components comprising propylbenzene (5 weight %), ethylmethylbenzenes (28 weight %), 1,3,5-trimethylbenzene (10 weight %), and 1,2,4-trimethylbenzene (32 weight %).

Aromatic 150 fluid comprises approximately fifty components with some of the principle components comprising about 1.7 weight % of 1,2,4-trimethylbenzene; about 3.0 weight % of 1,2,3-trimethylbenzene and meta-cumene; a mixture of about 81.6 weight % $C_{10}$ to $C_{12}$ benzene compounds, having one or more substituents selected from methyl, ethyl, propyl, and butyl; about 8.6 weight % naphthalene; and about 0.3 weight % methylnaphthalene.

Aromatic 200 fluid comprises approximately 25 to 30 components with some of the principle components comprising naphthalene (10 weight %); various alkylnaphthalenes (75 weight %), including 2-methylnaphthalene (26 weight %), 1-methylnaphthalene (13 weight %), 2-ethylnaphthalene (2 weight %), dimethyl naphthalenes (18 weight %), and trimethyl naphthalenes (7 weight %); and the remaining 15 weight % comprises primarily alkylbenzenes, as determined by gas chromatographic analysis.

Other solvents pertain to alcohols, such as methanol, ethanol, isopropanol, ether, acetone, benzene, chloroform, ethyl acetate, heptane, diethylether, n-pentane, kerosene, methyl isobutyl ketone, xylene, dimethylformamide, acetonitrile, methylethyl ketone, n-methyl pyrrolidone, ethylene glycol, turpentine, lionene, pinene, gamma butrolactone, methylene chloride or combinations thereof.

Suitable oil based solvents include, but are not limited to, for example, Guerbet alcohols based on fatty alcohols having 6 to 18, preferably 8 to 10, carbon atoms, esters of linear $C_6$-$C_{22}$-fatty acids with linear or branched $C_6$-$C_{22}$-fatty alcohols or esters of branched $C_6$-$C_{13}$-carboxylic acids with linear or branched $C_6$-$C_{22}$-fatty alcohols, such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_6$-$C_{22}$-fatty acids with branched alcohols, in particular 2-ethylhexanol, esters of $C_{16}$-$C_{38}$-alkylhydroxy carboxylic acids with linear or branched $C_6$-$C_{22}$-fatty alcohols, in particular Dioctyl Malate, esters of linear and/or branched fatty acids with polyhydric alcohols (such as, for example, propylene glycol, dimerdiol or trimertriol) and/or Guerbet alcohols, triglycerides based on $C_6$-$C_{10}$-fatty acids, liquid mono-/di-/triglyceride mixtures based on $C_6$-$C_{18}$-fatty acids, esters of $C_6$-$C_{22}$-fatty alcohols and/or Guerbet alcohols with aromatic carboxylic acids, in particular benzoic acid, esters of $C_2$-$C_{12}$-dicarboxylic acids with linear or branched alcohols having 1 to 22 carbon atoms (Cetiol® B) or polyols having 2 to 10 carbon atoms and 2 to 6 hydroxyl groups, vegetable oils, branched primary alcohols, substituted cyclohexanes, linear and branched $C_6$-$C_{22}$-fatty alcohol carbonates, such as, for example, Dicaprylyl Carbonate (Cetiol® CC), Guerbet carbonates, based on fatty alcohols having 6 to 18, preferably 8 to 10, carbon atoms, esters of benzoic acid with linear and/or branched $C_6$-$C_{22}$-alcohols (e.g. Cetiol® AB), linear or branched, symmetrical or asymmetrical dialkyl ethers having 6 to 22 carbon atoms per alkyl group, such as, for example, dicaprylyl ether (Cetiol® OE), ring-opening products of epoxidized fatty acid esters with polyols, silicone oils (cyclomethicones, silicone methicone grades, etc.), aliphatic or naphthenic hydrocarbons, such as, for example, squalane, squalene or dialkylcyclohexanes, and/or mineral oils.

As used herein, a composition or combination "consisting essentially" of certain ingredients refers to a composition including those ingredients and lacking any ingredient that materially affects the basic and novel characteristics of the composition or method. The phrase "consisting essentially of" excludes from the claimed compositions and methods additional antimicrobial agents; unless such an ingredient is specifically listed after the phrase.

As used herein, a composition or combination "substantially free of" one or more ingredients refers to a composition that includes none of that ingredient or that includes only trace or incidental amounts of that ingredient. Trace or incidental amounts can include the amount of the ingredient found in another ingredient as an impurity or that is generated in a minor side reaction during formation or degradation of the compositions employed in the present method.

For the purpose of this patent application, successful microbial reduction is achieved when the microbial populations are reduced by at least about 50%, or by significantly more than is achieved by a wash with water. Larger reductions in microbial population (e.g., at least about 99% reduction) provide greater levels of protection.

DETAILED DESCRIPTION

Reducing Population of Microbe

In other embodiments, the present invention relates to methods for reducing the population of a crop-related microbe. The method includes applying to an object a biofilm reducing agent, or a metal antimicrobial agent and a biofilm reducing agent. The method includes applying the agents together in one composition or separate compositions in amount and for time sufficient to reduce the microbial population. The metal antimicrobial agent may include copper or copper containing compounds. In one embodiment, provide is a composition that includes a carrier (e.g., water), and optionally a surfactant (e.g., Triton X-100 (octyl phenol alkoxylate n9.5) and Tectronic 1107 (alkoxylated ethylene diamine with, for example an average molecular weight of about 15,000), solvent (e.g., 1-methyl-2-pyrrolidinone), and optionally alcohol (e.g., ethanol).

In a specific embodiment, the crop is *citrus*, and the microbe is a canker microbe (e.g., *citrus* canker microbe) or microbes.

The method can include applying the biofilm reducing agent, or a metal antimicrobial agent and biofilm reducing agent, to any of a variety of objects, such as a *citrus* tree. The method can include applying the agents to *citrus* fruit. The *citrus* fruit can be on the tree or can be off the tree (i.e., it can already have been picked). The method can include applying the agents to inanimate objects, such as equipment. The equipment can be equipment used in a *citrus* orchard, equipment used for transporting or processing produce, such as *citrus* fruit, equipment used for transporting or processing a plant, or the like.

In a particular embodiment, provided is a method of reducing a population of a microbe on an object by applying a biofilm reducing agent and a metal antimicrobial agent to the object, such that efficacy of the metal antimicrobial agent is enhanced. Enhancement of the metal antimicrobial agent involves the achievement of efficacy of a lower dose of the metal antimicrobial agent in the presence of the biofilm reducing agent that requires a higher dose of the metal antimicrobial agent in the absence of the biofilm reducing agent. This embodiment allows for a reduction in the amount of metal antimicrobial agents needed to control microbe populations, which, in turn, is less harmful to the environment, less toxic, and reduces costs involved in controlling microbes.

Embodiments also relate to methods for treating *citrus* canker. The method may include applying to a *citrus* tree a biofilm reducing agent, or a metal antimicrobial agent and a biofilm reducing agent. The method includes applying the antimicrobial composition in amount and for time sufficient to reduce the microbial population.

Embodiments also relate to methods and compositions for reducing the population of canker microbe (e.g., *citrus* canker microbe). Such a composition includes a biofilm reducing agent, or a metal antimicrobial agent and a biofilm reducing agent. The composition can be for applying to an object subject to contamination with canker microbe (e.g., *citrus* canker microbe). In another embodiment, a biofilm reducing agent is applied alone or separate to a metal antimicrobial agent. For example, a composition that includes biofilm reducing agent to reduce population of a canker microbe without an antimicrobial agent (such as a metal antimicrobial agent is applied to a *citrus* tree.

Embodiments also relate to articles of manufacture. Such an article of manufacture can include a composition including a biofilm reducing agent or a metal antimicrobial agent and a biofilm reducing agent. Such an article of manufacture can include a sprayer configured for spraying *citrus* and a composition including metal antimicrobial agent and a biofilm reducing agent. Suitable sprayers configured for spraying *citrus* include those large enough to be towed behind a truck and that, for example, use air in forming a spray from a composition in a tank or other container. Suitable sprayers include electrostatic sprayers. Such an article of manufacture can include composition including a biofilm agent, or a metal antimicrobial agent and a biofilm reducing agent, and instructions for applying the composition to *citrus*. Such an article of manufacture can include composition including metal antimicrobial agent and a biofilm reducing agent and instructions for applying the composition to object subject to contamination with canker microbe (e.g., *citrus* canker microbe).

Any of a variety of known methods can be employed for testing for activity against a canker microbe (e.g., *citrus* canker microbe). For example, a composition can be tested in a laboratory test (e.g., in vitro) or a nursery. Embodiments of such methods are described in the Examples.

For example, a composition can be tested in a prevention fruit protocol. A prevention fruit protocol can employ *citrus* fruit (non-waxed) treated with 50 ppm sodium hypochlorite and rinsed with sterilized Milli-Q water. The method can include treating a fruit surface by spraying a solution of the test substance over the fruit surface with a spray bottle several times over one week. Infecting the fruit can be carried out by misting *Xanthomonas* (e.g., *X. citri*) or a model microorganism over surface or by spot inoculation (especially to vulnerable areas). This can be followed by allowing bacteria to sit on the fruit overnight. The fruit can be treated with the test substance. The fruit can be incubated in a hood for about 2 to about 3 weeks to determine if there is growth. The fruit can be sampled after the incubation period by putting the fruit into neutralizer (bag), massaging for one minute, and plating. Controls can include fruit treated with chemicals for the first treatment period, inoculated with no follow-up treatment, and fruit untreated with chemicals but inoculated.

Washing *Citrus* with Anti-*Citrus* Canker Compositions

According to other embodiments, provided are methods of treating and using water-based systems for transporting, processing, and/or washing *citrus*. Also provided are methods for transporting or processing *citrus* using an aqueous medium to transport the *citrus* through, for example, one or more processing steps and environments. According to one embodiment, the aqueous medium includes a metal antimicrobial agent and a biofilm reducing agent. In addition, provided is a method for reducing the population of microbes in aqueous streams by applying or incorporating a biofilm reducing agent, or a metal antimicrobial agent and a biofilm reducing agent, to or into the aqueous stream. Generally, the aqueous streams used in any number of applications such as the application of streams for the transport of *citrus* into the processing environment and through the various steps of processing.

In a further method embodiment, after picking, the method includes transporting and/or washing *citrus* in a stream of a biofilm reducing agent composition, or a metal antimicrobial agent and a biofilm reducing agent composition. For example, an aqueous metal antimicrobial agent and biofilm reducing agent composition can be used to support or transport the *citrus* from an unloading site to a storage, packing, or processing location. The method can include introducing the *citrus* into a flume containing an aqueous metal antimicrobial agent and a biofilm reducing composition.

In a further embodiment, provided is a method that includes transporting fresh *citrus* in and to food handling equipment used at a processing plant using a stream of a biofilm reducing agent, or a metal antimicrobial agent and biofilm reducing agent composition. For example, the method can include transporting a food item using or in a biofilm reducing agent composition, or a metal antimicrobial agent and biofilm reducing agent composition, from an initial location through a series of individual processing stages to a station where the *citrus* is removed from the water and packed. The method can include recycling the aqueous biofilm reducing agent composition, or aqueous metal antimicrobial agent and biofilm reducing agent composition used for transporting or processing *citrus*.

In a further embodiment, provided is a method of cleaning (e.g., washing), cooling (e.g., in a bath), heating, cooking, or otherwise processing the *citrus* before packaging using a biofilm reducing agent composition, or an metal antimicrobial agent and a biofilm reducing agent. In an embodiment, the present method includes transporting and processing the *citrus* using the same stream. In a specific embodiment, the present method includes transporting the *citrus* in a first aqueous stream and processing the *citrus* in a second aqueous composition distinct from the transport stream. The present invention includes recycling the aqueous metal antimicrobial agent and biofilm reducing agent employed in methods for cleaning, cooling, heating, cooking, or otherwise processing the *citrus*.

In another embodiment, disclosed is a method of reducing the population of microbes on or in the water, flume, or other transport or processing equipment employed with the *citrus*. The method includes contacting the water, flume, or other transport or processing equipment with a biofilm reducing agent, or a metal antimicrobial agent and a biofilm reducing agent. In an embodiment, the present invention includes reducing or preventing the buildup of slime or biofilm on surfaces of the flume or other transport or processing equipment employed with the *citrus*. The method includes contacting the surfaces of the flume or other transport or processing equipment with a metal antimicrobial agent and biofilm reducing agent.

The present invention also includes methods for packaging *citrus*. In an embodiment, the present method can reduce the microbial population on *citrus* or packaging material before or during the packaging operation. The method includes contacting the *citrus* or packaging material with a biofilm reducing agent, or a metal antimicrobial agent and a biofilm reducing agent before or during the packaging operation. In an embodiment, the present method can reduce the microbial population on packaged *citrus*. The method includes contacting the package of *citrus* with metal antimicrobial agent and biofilm reducing agent.

Embodiments include transporting or processing packaged *citrus* using the biofilm reducing agent, or a metal antimicrobial agent and biofilm reducing agent composition. In an embodiment, the present method includes heating, cooling, or otherwise processing packaged *citrus* using a metal antimicrobial agent and biofilm reducing agent.

In an embodiment, the present disclosure includes a method of reducing the population of microbes on *citrus*. The method can include contacting the *citrus* with a biofilm reducing agent, or a metal antimicrobial agent and a biofilm reducing agent. Contacting can include applying the present composition to the *citrus*. Applying can occur at any step of the life cycle, production cycle, or marketing of the *citrus*. For example, the present composition can be applied to the *citrus* in the field, in or on any apparatus (e.g., harvester), in a transport apparatus or during transport, in a warehouse, in a processing facility, in a wholesaler, in a retail establishment (e.g., a grocer), in a home, or in a restaurant. In a specific embodiment, applying a biofilm reducing agent, or a metal antimicrobial agent and a biofilm reducing agent, involves injecting into a trunk of a tree, administering to bark of a tree, administering to soil proximate to a tree, or irrigating a tree. Proximate to the tree involves a distance immediately adjacent to the tree or at distance from the tree no more than what is sufficient to exact benefits of the composition. In one example, proximate means within ten feet, within 20 feet, within 30 feet, within 40 feet, within 50 feet or within 60 feet from the tree.

Once the biofilm agent, or metal antimicrobial agent and biofilm reducing agent, are applied to any given transport stream, the biofilm agent or antimicrobial agent will be subjected to a demand resulting from microbes present in the stream as well as optionally added organic or inorganic material present in the stream. As a general guideline, not limiting of the invention, the present invention includes the concentrations of metal antimicrobial agent and biofilm reducing agent containing composition found after demand.

Embodiments of the methods of the present invention can include agitation or sonication of the use composition, particularly as a concentrate is added to water to make the use composition. In an embodiment, the present methods include water systems that have some agitation, spraying, or other mixing of the solution. The *citrus* can be contacted with the compositions of the invention effective to result in a reduction significantly greater than is achieved by washing with water, or at least a 50% reduction, at least a 90% reduction, or at least a 99% reduction in the resident microbial preparation.

The present methods can employ a certain minimal contact time of the composition with of *citrus* for occurrence of significant antimicrobial effect. The contact time can vary with concentration of the use composition, method of applying the use composition, temperature of the use composition, amount of soil on the *citrus*, amount of soil in the aqueous stream, number of microorganisms on the *citrus*, number of microorganisms in the aqueous stream, or the like. Contact time in the field can be for as long as nature allows, for example, until the next rain or heavy rain. In an embodiment, the exposure time is at least about 5 to about 60 seconds. In a further embodiment, exposure time is at least 5 minutes, at least 1 hour, at least 6 hours, or at least 24 hours.

Electrostatic Sprayers and Spraying

In another alternative embodiment of the present invention, the *citrus* or other plants can be treated with an electrostatically charged spray of a composition including a biofilm agent, or a metal antimicrobial agent and a biofilm reducing agent or coadministration of separate compositions containing one or the other agents. The composition can be spray applied as charged droplets by using conventional electrostatic spray technologies including inductively charged methodologies. As charged droplets, the composition will be attracted to opposite or differentially charged surfaces such as the surface of the *citrus* or other plants. As a result, more composition can be applied to the *citrus* and less solution will miss the intended target, commonly called over-spray. The charged droplets can provide an evenly distributed solution layer on the plants. The charged droplet size can range from about 10 microns to about 500 microns.

Adjuvants

The antimicrobial composition of the invention can also include any number of adjuvants. Specifically, the composition of the invention can include additional antimicrobial agent, wetting agent, defoaming agent, thickener, a surfactant, foaming agent, aesthetic enhancing agent (i.e., colorant (e.g., pigment), odorant, or perfume), among any number of constituents which can be added to the composition, or combinations of the foregoing. In exemplary embodiments, an adjuvant is any material that when added to a spray solution enhances or modifies the action of a pesticide. A surfactant is a class of adjuvant including any compound which possesses distinct hydrophilic and lipophilic regions, which allow it to reduce the surface tension when mixed with water. Example chemical classes include, but are not be limited to: Alcohol alkoxylates, Alkylaryl ethoxylates, Fatty amine ethoxylates, Organosilicones, Some surfactants include multiple active constituents.

In addition to surfactants, other types of adjuvants would include oils (petroleum and crop based), acidifiers, buffers, and others.

Adjuvants can be preformulated with the antimicrobial composition of the invention or added to the system simultaneously, or even after, the addition of the antimicrobial composition. Composition embodiments can also contain any number of other constituents as necessitated by the application, which are known and which can facilitate the activity of the present invention.

Additional Antimicrobial Agent

The antimicrobial compositions of the invention can contain an additional antimicrobial agent. Additional antimicrobial agent can be added to use compositions before use. Suitable antimicrobial agents include, but are not limited to, peroxycarboxylic acid (e.g., medium chain (e.g., C5-C12, C6 to C10, or C8) peroxycarboxylic acid or mixed medium chain and short chain (e.g., C2-C4) peroxycarboxylic acid (e.g., C2 and C8)), carboxylic esters (e.g., p-hydroxy alkyl benzoates and alkyl cinnamates), sulfonic acids (e.g., dodecylbenzene sulfonic acid), iodo-compounds or active halogen compounds (e.g., elemental halogens, halogen oxides (e.g., NaOCl, HOCl, HOBr, $ClO_2$), iodine, interhalides (e.g., iodine monochloride, iodine dichloride, iodine trichloride, iodine tetrachloride, bromine chloride, iodine monobromide, or iodine dibromide), polyhalides, hypochlorite salts, hypochlorous acid, hypobromite salts, hypobromous acid, chloro- and bromo-hydantoins, chlorine dioxide, and sodium chlorite), organic peroxides including benzoyl peroxide, alkyl benzoyl peroxides, ozone, singlet oxygen generators, and mixtures thereof, phenolic derivatives (e.g., o-phenyl phenol, o-benzyl-p-chlorophenol, tert-amyl phenol and $C_1$-$C_6$ alkyl hydroxy benzoates), quaternary ammonium compounds (e.g., alkyldimethylbenzyl ammonium chloride, dialkyldimethyl ammonium chloride and mixtures thereof), aminoglycosides (Streptomycin, kasugamycin), tretracyclines (oxytetracycline), *Bacillus* biologicals (*Bacillus subtilis, Bacillus amyloliquefaciens*), *Pantoea* biologicals (*Pantoea agglomerans*), *Pseudomonas* biologicals (*Pseudomonas fluorescens*), Bacteriophages (many phage strains), and mixtures of such antimicrobial agents, in an amount sufficient to provide the desired degree of microbial protection.

The present composition can include an effective amount of additional antimicrobial agent, such as about 0.001 wt-% to about 60 wt-% antimicrobial agent, about 0.01 wt-% to about 15 wt-% antimicrobial agent, or about 0.08 wt-% to about 2.5 wt-% antimicrobial agent.

Use Compositions

The present compositions may include concentrate compositions and use compositions. For example, a concentrate composition can be diluted, for example with water, to form a use composition. In an embodiment, a concentrate composition can be diluted to a use solution before to application to an object. For reasons of economics, the concentrate can be marketed and an end user can dilute the concentrate with water or an aqueous diluent to a use solution.

The level of active components in the concentrate composition is dependent on the intended dilution factor and the desired activity of the composition components. Generally, a dilution of about 1 fluid ounce to about 20 gallons of water to about 5 fluid ounces to about 1 gallon of water is used for aqueous antimicrobial compositions. Higher use dilutions can be employed if elevated use temperature (greater than 25° C.) or extended exposure time (greater than 30 seconds) can be employed. In the typical use locus, the concentrate is diluted with a major proportion of water using commonly available tap or service water mixing the materials at a dilution ratio of about 3 to about 20 ounces of concentrate per 100 gallons of water. For example, the use composition can include Surf acme diluted 1:2, 1:4 or 1:8.

For example, a use composition can include about 0.01 to about 4 wt-% of a concentrate composition and about 96 to about 99.99 wt-% diluent; about 0.5 to about 4 wt-% of a concentrate composition and about 96 to about 99.5 wt-% diluent; about 0.5, about 1, about 1.5, about 2, about 2.5, about 3, about 3.5, or about 4 wt-% of a concentrate composition; about 0.01 to about 0.1 wt-% of a concentrate composition; or about 0.01, about 0.02, about 0.03, about 0.04, about 0.05, about 0.06, about 0.07, about 0.08, about 0.09, or about 0.1 wt-% of a concentrate composition. Amounts of an ingredient in a use composition can be calculated from the amounts listed above for concentrate compositions and these dilution factors.

The administration of a metal antimicrobial agent and biofilm reducing agent can be conducted by application of a composition containing both components or by coadministration of two or more compositions containing either of the agents. Typically, administration will involve the application of the metal antibiotic agent and the biofilm reducing agent such that they are both present on the intended object contemporaneously. Alternatively, as noted above, administration involves application of a biofilm reducing agent without administration of a metal antimicrobial agent.

The present invention may be better understood with reference to the following examples. These examples are intended to be representative of specific embodiments of the invention, and are not intended as limiting the scope of the invention.

EXAMPLES

A. Materials and Methods

Bacterial Strains and Culture Conditions.

Xac strain 306 [rifamycin (Rif) resistant] (Rybak et al., 2009) was used. Nutrient agar (NA) and Nutrient broth (NB) were as the media for the growth of Xac. The bacterium was initially streaked from −80° C. glycerol stock on a NA plate and a fresh single colony was inoculated in NB (40 ml) in 150 ml flasks and cultured at 28° C. with agitation at 200 r.p.m. The overnight cultures were diluted in NB to standardize the cultures to obtain an optical density at 600 nm ($OD_{600}$) of 1.0 prior to setting up the biofilm assay and cell growth measurements. When necessary, rifamycin was added in the medium at a final concentration of 50 mg/mL.

Preparation of Test Compounds.

D-amino acids (D-alanine, D-leucine, D-methionine, D-serine, D-tryptophan, and D-tyrosine) and indole derivatives [3-indoleacetic acid (IAA), 3-indolylacetonitrile (IAN) and indole-3-propioninc acid (I3PA)] from plant sources were purchased from Sigma-Aldrich Co. (Missouri, USA). The other chemicals including crystal violet (CV), ethyl alcohol, dimethyl sulfoxide (DMSO) were purchased from Fisher Scientific Co. (Pittsburgh, USA). Stock solutions (500 mM in double distilled water for D-amino acids; 5 mg/mL in 1% DMSO for indole derivatives) were filter sterilized and stored at −20° C. and diluted in sterilized distilled water (SDW) or DMSO for the initial test concentrations.

Evaluation of D-Amino Acids and Indole Derivatives for Potential Biofilm Inhibition Ability.

A static biofilm formation assay in 96-well polystyrene plates coupled with CV staining was performed as previously reported with modifications (Li and Wang, 2011). Briefly, a 96-well polystyrene plate (Nunclon surface, Nuncbrand, Denmark) was prepared with 170 μL NB plus 1.0% glucose per well. Aliquots of 20 μL each of the different concentrations of the tested compound were pipetted into eight wells containing 170 μL of NB plus 1.0% glucose. To each of these wells was added 10 μL of the standardized overnight Xac 306 culture ($OD_{600}$=1.0). Control wells contained NB plus 1.0% glucose and SDW or 0.1% DMSO as a sterility control, or standardized overnight Xac 306 culture as a growth control. The plate was covered by a MicroWell lid (Nunclon), sealed with parafilm to prevent evaporation and incubated at 28° C. for 48 h without shaking. After incubation, the planktonic growth was measured at $OD_{600}$. To quantify the amount of biofilms formed on the surfaces of the wells, the culture was removed from the wells. After drying, the wells were washed twice with 200 μl of SDW for 5 min, allowed to dry then 200 μl of 0.1% CV added. After 30 minutes, the CV was removed. The wells were washed with excess SDW to remove unbound CV and air dried in an inverted position for 2 h. Afterward, 200 μl of 95% ethanol was added to the wells and incubated for 30 min at room temperature to elute bound CV. The eluted CV was 2-fold diluted in double distilled water and the absorbance at 590 nm was measured. Each data point was averaged from eight replicate wells.

To gain further evidence of the effect of selected compounds on biofilm formation, biofilm formation in glass tubes and on leaf surfaces was examined as described previously (Li and Wang, 2012). Briefly, the standardized overnight culture of Xac 306 ($OD_{600}$=1.0) were diluted 1:10 in fresh NB containing 1.0% glucose and the selected compound. For biofilm formation assay in glass tubes (Fischer Scientific, Pittsburgh, Pa.), 1 ml of the diluted bacterial suspension was transferred into each sterilized borosilicate glass tube and incubated at 28° C. without shaking for 48 h. The planktonic growth was then discarded and the tubes were gently washed three times with SDW. The biofilm formed on the tubes was visualized by staining with 0.1% CV. The stain remaining in cells on glass tubes was dissolved in 95% ethanol and quantified by measuring the optical density at 590 nm. For biofilm formation assay on leaf surfaces, 20 μl of the diluted bacterial suspension was dropped onto the abaxial surface of *citrus* leaves. The leaves were kept in a humidified chamber at 28° C. for 24 h without shaking. The biofilm formed on the leaf surfaces was visualized by staining with 0.1% CV. The biofilm assays were repeated three times with four replicates each time.

Determination of Minimum Inhibitory Concentrations (MICs).

Xac strain 306 was grown in NB at 28° C. with shaking at 200 rpm for 7 h. The cultures were standardized to an $OD_{600}$ of 0.03 ($5\times10^7$ colony forming unit (CFU)/mL) in NB and then aliquoted into wells of a 96-well plate, 190 μL per well. The initial test concentrations of the compounds were diluted (1:20) in the culture (10 μl of compound in 190 μl of culture) and incubated at 28° C. under stationary conditions. The cultures were monitored at 24 and 48 h at $OD_{600}$, and the lowest concentration resulting in no growth after 48 h compared to the control samples was defined as the MIC for Xac strain 306. All determinations were conducted in eight replicate wells and repeated three times.

Evaluation of Resistance of Xac Biofilm Cells to Copper.

The level of copper resistance of biofilms was evaluated using a cell viability assays. Briefly, Xac biofilms were prepared using NB with stationary incubation in glass tubes as described above. After 48 h-incubation, the cultures were removed and bacterial cells attached to the tubes were gently washed three times with SDW. One milliliter of fresh NB with $CuSO_4$ (1.0 mM), D-leucine (10 mM) or IAN (100 μg/mL), or a combination of these compounds was added to each tube. NB alone was used as control. Tubes were kept at room temperature for 24 h and shaken vigorously for 5 min. The suspensions were diluted in 10-fold series, and 10 μL of each dilution spotted in triplicate on NA plate. Plates were incubated at 28° C. for 48 to 72 h prior to assessing bacterial growth. Colonies that grew near the dilution endpoint were counted and bacterial populations in the initial suspensions prior to dilution were calculated. Each treatment compromises four replicates and the experiment repeated three times.

RNA Prepare and Quantitative Real-Time Reverse Transcription Polymerase Chain Reaction (qRT-PCR).

To investigate the mechanisms of D-leucine and IAN inhibiting Xac 306 biofilm formation, qRT-PCR analysis was used to determine differential gene expression for Xac306 cells with and without IAN (100 μg/mL) or D-leucine (10 mM). For this analysis, Xac306 was cultured in NB medium with or without biofilm inhibitor at 28° C. without shaking. Cells were collected after 48 h of incubation by centrifugation at 12,000×g for 5 min at 4° C. and used for RNA extraction. For the analysis of gene expression in Xac 306 planktonic and biofilm cells with sub-MICs $CuSO_4$ concentrations, we followed the same procedure described for evaluation of resistance of Xac biofilm cells to copper in glass tubes. Both biofilm cells attached to the glass tube at the medium-air interface and planktonic cells in culture were used. Cells collected after 48 h of incubation in the presence of $CuSO_4$ were washed by centrifugation at 12,000×g for 5 min at 4° C. with diethylpyrocarbonate treated water. Cells collected from five tubes were combined and served as one biological replicate. The pellet was stored at −80° C. until RNA extraction. Total RNA of Xac306 cells was isolated using RNA protect bacterial reagent (Qiagen, Valencia, Calif.) and RNeasy Mini Kit (Qiagen, Valencia, Calif.), following the manufacturer's instructions. The contaminated genomic DNA was removed using a TURBO DNA-free kit (Ambion, Austin, Tex.). RNA purity and quality were evaluated with a NanoDrop ND-1000 spectrophotometer (NanoDrop Technologies, Wilmington, Del.).

A one-step QRT-PCR was conducted using a 7500 fast real-time PCR system (Applied Biosystems, Foster City, Calif.) with a QuantiTect SYBR green RT-PCR kit (Qiagen, Valencia, Calif.) following the manufacturer's instructions. The gene specific primers (Table 1) were designed based on the genome sequence of Xac strain 306 (da Silver et al., 2002). In the biofilm inhibition mechanism studies, those primers targeted fifteen genes that were previously identified to be related bioflim formation in Xac strain 306 (Li and Wang, 2011). In the copper resistance analysis, those primers targeted the gum genes gumB and gumD polysaccharides—related gene galU, and copper resistance-related genes copA and copB (Teixeira et al., 2008; Behlau et al., 2012). The DNA gyrase subunit A encoding gene gyrA was used as endogenous control. The relative fold change in gene expression was calculated using the formula $2^{-\Delta\Delta CT}$ (Livak and Schmittgen, 2001). qRT-PCR was repeated twice with four independent biological replicates each time.

Plant Test in Greenhouse.

The effect of selected biofilm inhibitors on Xac infection/virulence-was investigated using 20-week-old potted grapefruit (*Citrus paradise* cv. Duncan grapefruit) plants in a quarantine greenhouse at the *Citrus* Research and Education Center, Lake Alfred, Fla. Copper ($CuSO_4$, 100 μg/mL), D-leucine (10 mM), IAN (100 μg/mL) and a combination of these compounds were individually prepared in 100 ml of SDW. Bacterial inoculum was prepared by growing Xac 306 on NA plates at 28° C. for 48 h, suspending in SDW, adjusting concentration to approximately $OD_{600}$=0.3 ($5\times10^8$ CFU/mL). The inoculation was performed by a spray method as described previously (Li and Wang, 2012) with modifications. Briefly, the abaxial surfaces of fully expanded, immature leaves of each plant were sprayed with the following treatments: SDW, Xac 306, and Xac 306 combined with $CuSO_4$ (100 μg/mL), D-leucine (10 mM), IAN (100 μg/mL), or a combination of these compounds. Silwett-L77 (silicone-polyether copolymer, Fisher) was added to each treatment at a 0.03% (V/V) final concentration. After inoculation, the plants were covered with plastic bags for 24 h to maintain a high (>90%) relative humidity and then kept in a greenhouse (approximately 60% relative humidity) for symptom development. All inoculations included a minimum of three immature leaves at a similar developmental stage from each plant, and each treatment comprised four plants. The experiments were repeated three times independently. SDW was applied as a negative control, and Xac306 mixed with SDW as positive control. To determine whether the timing of application of biofilm inhibitors in relation to Xac306 affected canker symptom suppression, the biofilm inhibitors were inoculated on leaves 6 h prior to or after inoculation with Xac306.

For bacterial population assays, the leaves of grapefruit plants were inoculated as described above. Two leaf discs randomly selected from each of three inoculated leaves were cut with a cork borer (0.8 cm in diameter) and then ground in 1 mL of SDW. The suspensions were serially diluted and plated on NA plates containing rifamycin. After incubation at 28° C. for 48 h, bacterial colonies were counted and the number of CFU per square centimeter of leaf tissue was calculated. The assays were repeated three times independently.

B. Results

D-Leucine and 3-Indolylacetonitrile (IAN) are Potent Biofilm Inhibitors of Xac

Figure 1C:
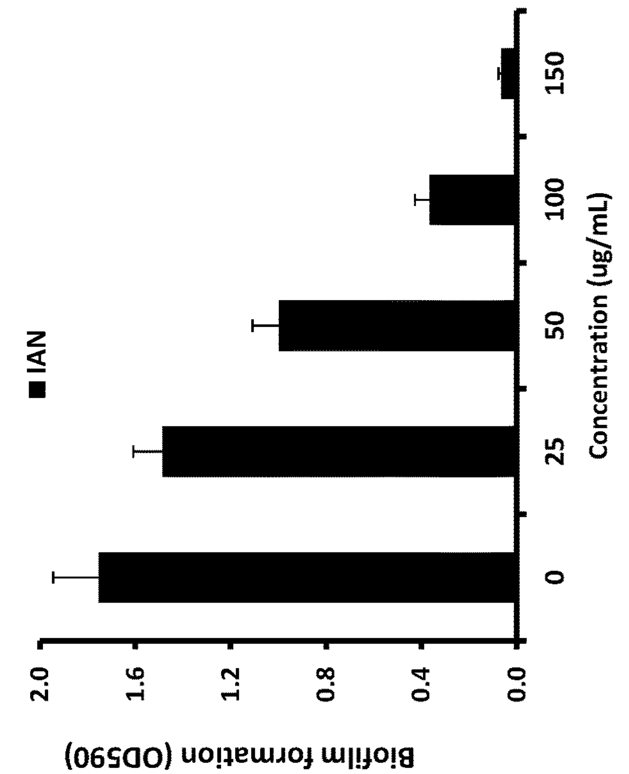
Figure 1B:
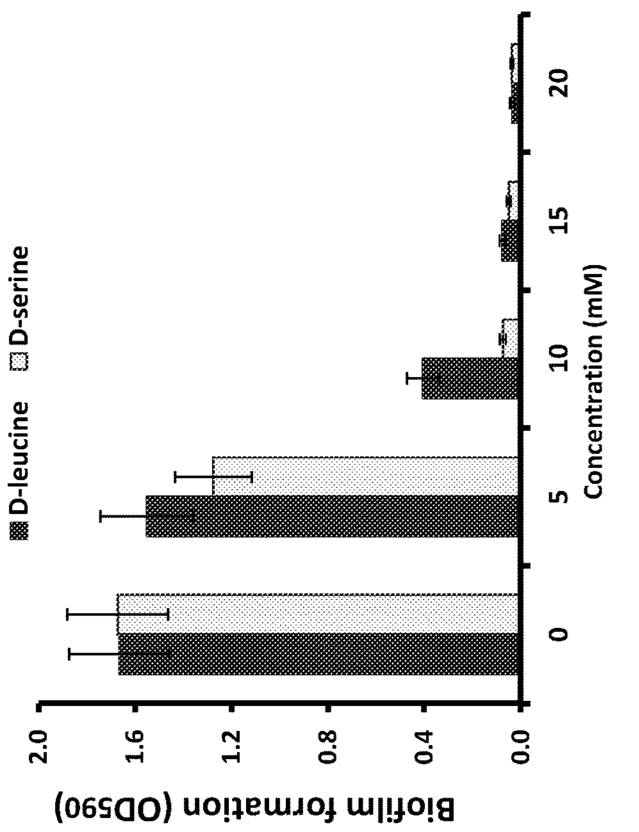

Six D-amino acids and three indole derivatives derived from plant sources were tested for their ability to inhibit biofilm formation of Xac306 in 96-well plate biofilm assays. In the absence of D-amino acid or indole derivative, Xac306 formed robust biofilms (FIG. 1A). D-leucine, D-serine and IAN significantly reduced Xac306 biofilm formation by 55 to 70%, whereas the other D-amino acids or indole derivatives tested did not affect Xac306 biofilm formation (FIG. 1A). Furthermore, the compounds D-leucine, D-serine and IAN decreased Xac306 biofilm in a dose-dependent manner from 0 to 20 mM for D-leucine and D-serine (FIG. 1B) and 0 to 150 μg/mL for IAN (FIG. 1C).

To test the toxicity of the three biofilm inhibitors, the MICs were determined in NB medium. The results showed that D-serine had the lowest MIC of 8.0 mM, followed by D-leucine and IAN, with MICs of 16.0 mM and 200 μg/mL respectively (Table 2). D-leucine and IAN had relatively high MICs but paradoxically demonstrated the potent decrease in biofilm mass (58% decrease for D-leucine; 65% decrease for IAN) at lower concentrations than MICs (10 mM for D-leucine and 100 μg/mL for IAN) (FIG. 1A). Due to its low toxicity to Xac306 and apparent potency against biofilm formation, D-leucine and IAN were selected for further studies.

Figure 2:
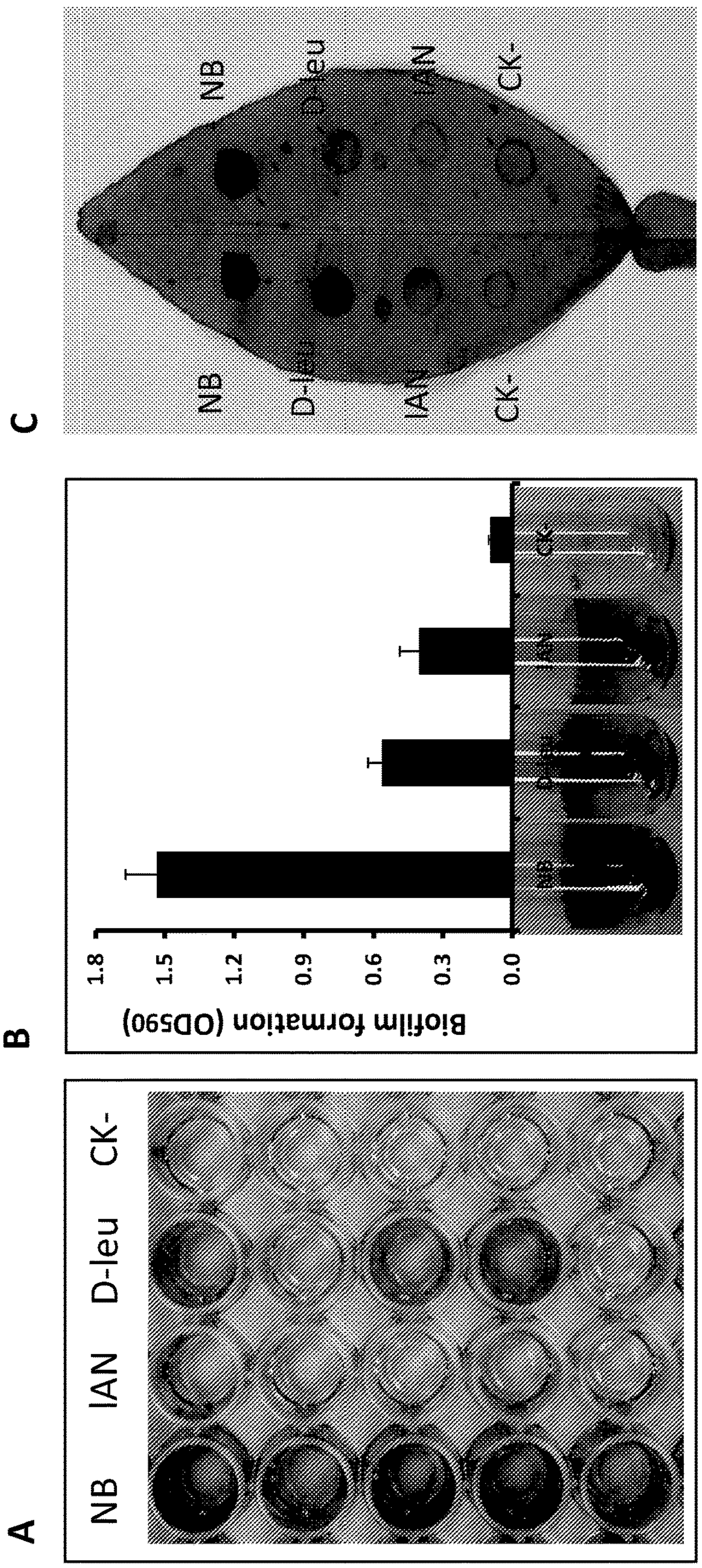
FIG. 2A-FIG. 2C Biofilm formation by *X. citri* subsp. *citri* strain 306 on different surfaces. Biofilm formation in polystyrene 96-well plates (A), glass tubes (B) and on *citrus* abaxial leaf surfaces (C) was visualized using crystal violet staining. Biofilm formations in glass tubes were quantified by measuring the optical density at 590 nm after dissolution in 95% ethanol. NB: NB medium; D-leu: D-leucine (10 mM); IAN: 3-indolylacetonitrile (100 μg/mL); CK-: NB medium without inoculation of strain 306. All experiments were performed in four replicates and repeated three times with similar results, and only one representative result is presented. Means±standard deviations were shown.

D-Leucine and IAN Reduce Biofilm Formation on Abiotic Surfaces and Host Leaves at Sub-MIC Concentrations To further evaluate and confirm the antibiofilm properties of D-leucine and IAN, biofilm formation of Xac306 with the compounds at sub-MIC (10 mM for D-leucine and 100 μg/mL for IAN), a concentration that does not significantly decrease planktonic cell density (data not shown), was examined on three different kinds of surfaces: polystyrene, glass and host leaves. The D-leucine or IAN treated cultures exhibited a significant reduction in biofilm formation both on polystyrene surface and in glass tubes compared to the untreated control, where the level of biofilm formation were reduced to 50% and 60% of control, respectively (FIG. 2 A; B). Similar to the observations on polystyrene surface and in glass tubes, the D-leucine or IAN treated cultures showed declined biofilm formation on *citrus* leaf surfaces (FIG. 2 C), suggesting that D-leucine and IAN reduced biofilm formation of Xac strain 306 on *citrus* leaves. These findings confirmed that D-leucine and IAN had specific activity inhibiting biofilm formation by Xac strain 306.

Differential Gene Expression of Xac 306 Cells with IAN

Figure 3:
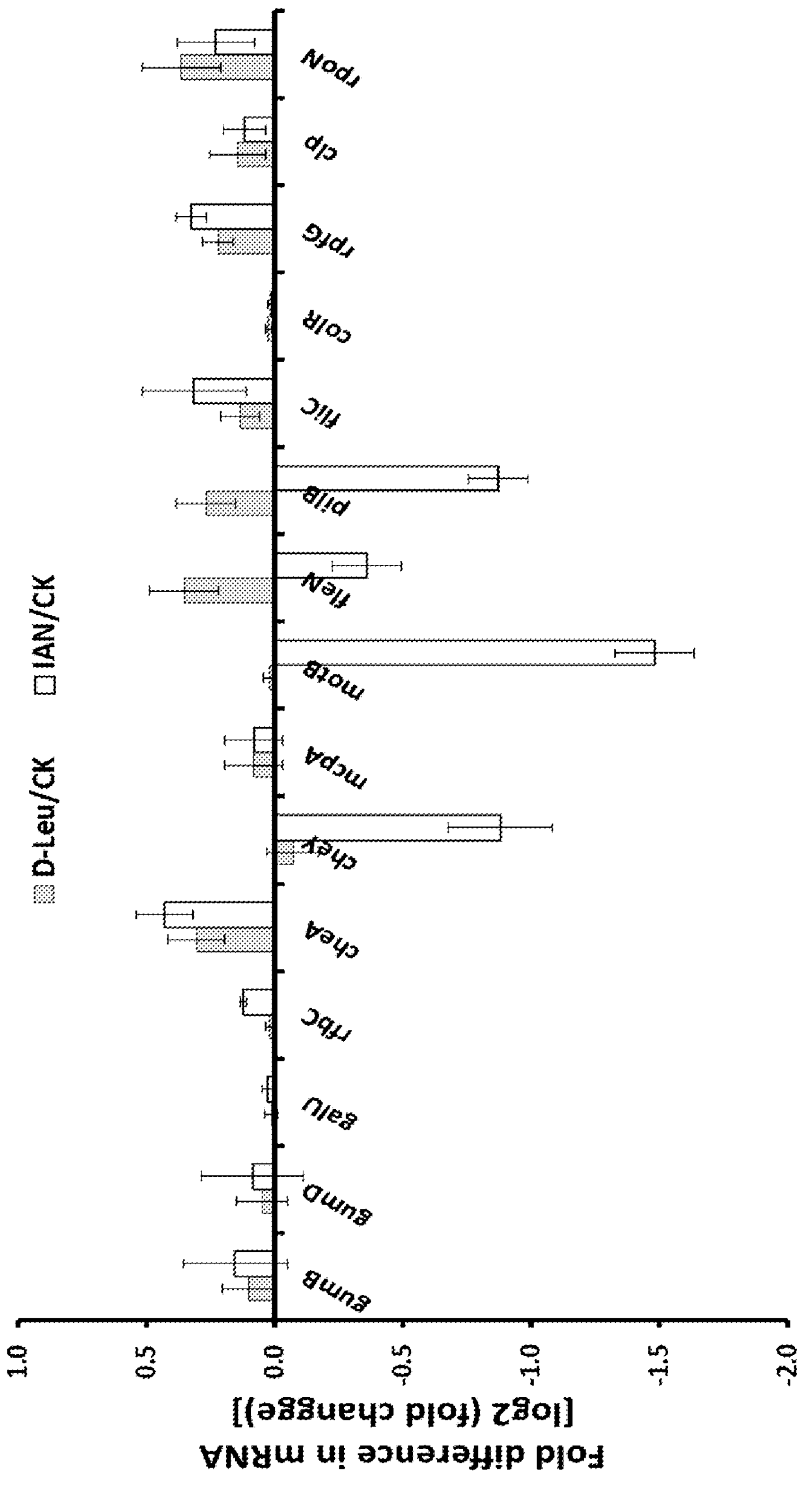
FIG. 3 Differential gene expression in *X. citri* subsp. *citri* strain306 cells in the presence of IAN at 100 μg/mL as revealed by qRT-PCR analysis. Data were presented as ratio of transcript number IAN compared with the untreated control. gyrA was used as endogenousa control. The asterisk denotes $P<0.05$ (t-test) compared with the untreated control. qRT-PCR was repeated twice with similar results with four independent biological replicates each time.

To obtain insight into the mechanisms by which D-leucine and IAN inhibit biofilm formation, the effect of these two compounds was evaluated on expression of genes important for biofilm formation in Xac 306 using qRT-PCR. The selected genes included the gum genes gumB and gumD, polysaccharides—related gene galU, O-antigen biosynthesis gene rfbC, chemotaxis and motility genes cheA, cheY, mcpA, and motB, type IV twitching motility gene pilB, flagellar biosynthesis genes fleN and fliC, and regulator genes colR, clp, rpfG and rpoN. The results showed significantly ($p<0.05$, student t-test) repression of chemotaxis and motility genes cheY, motB and pilB with IAN, whereas no induction or repression of any of the tested genes by D-leucine (FIG. 3).

Suppression of Xac 306 Resistance to Copper by D-Leucine and IAN

The copper resistance levels of planktonic cells of Xac306 were evaluated with and without biofilm inhibitor, respectively. In the NB medium, planktonic cells exhibited a MIC of 0.50 mM $CuSO_4$ without biofilm inhibitor. In the presence of D-leucine, IAN or a combination of the two compounds at a sub-MIC concentration (10 mM for D-leucine and 100 μg/mL for IAN), the MICs of $CuSO_4$ against Xac 306 planktonic cells were decreased to 0.25 mM (Table 2). These results suggested that D-leucine and IAN increased the susceptibility of Xac 306 planktonic cells to copper under the applied conditions.

Figure 4:
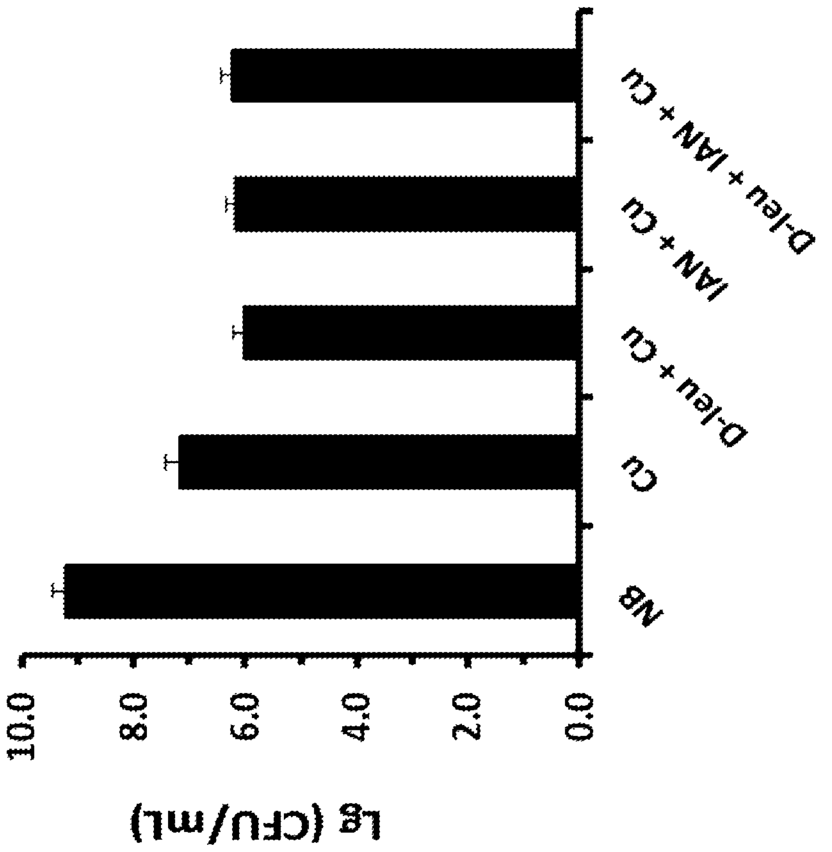
FIG. 4. Effect of D-leucine and IAN on cell viability of *X. citri* subsp. *citri* strain306 biofilms exposed to copper. Viable cells in biofilms exposed to the agent alone or in combination were quantified using the dilution-plating method. Cu: $CuSO_4$ (1.0 mM); D-leu: D-leucine (10 mM); IAN: 3-indolylacetonitrile (100 g/mL); NB: NB medium alone. The experiments were repeated three times with similar results with four replicates. The error bars indicated standard deviations.

In the cell viability assays, biofilms treated with D-leucine, IAN or a combination of the two compounds at sub-MIC concentrations (10 mM for D-leucine and 100 μg/mL for IAN) were about 10 times more susceptible to $CuSO_4$ than the untreated control. The cell viability of Xac biofilms exposed to $CuSO_4$ (1.0 mM) was significantly reduced by D-Leucine or IAN. Biofilms exposed to $CuSO_4$ (1.0 mM) alone for 24 h contained an average of $3\times10^7$ CFU/mL, while the biofilms treated by D-leucine (10.0 mM), IAN (100 μg/ml) or a combination of the two compounds contained an average of $1.1\times10^6$, $4.3\times10^6$, and $2.5\times10^6$ CFU/mL, respectively (FIG. 4). These findings indicated that D-leucine and IAN increased the susceptibility of Xac 306 biofilm cells to copper under the applied conditions.

To obtain insight into the mechanisms by which D-leucine and IAN increase the susceptibility of Xac 306 cells to copper, evaluated was the effect of the two compounds on expression of the polysaccharides related gene galU, gum genes gumB and gumD, and copper resistance related genes copA and copB in Xac306 planktonic and biofilm cells, respectively. The qRT-PCR results showed that either D-leucine or IAN did not affect express of any of the gene tested in Xac planktonic or biofilm cells in the presence of $CuSO_4$ (data not shown).

Figure 5:
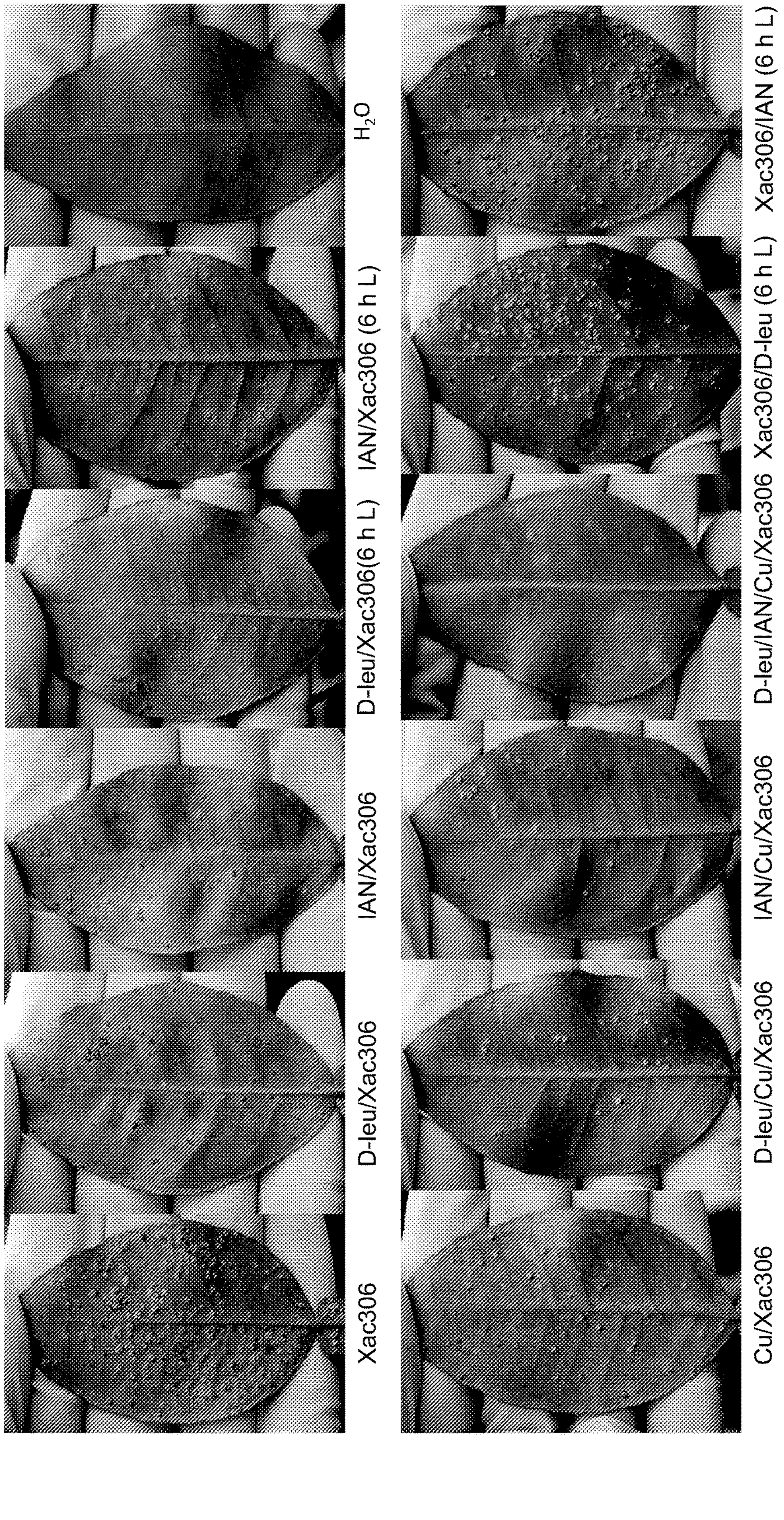
FIG. 5A-FIG. 5B Effect of D-leucine and IAN on *X. citri* subsp. *citri* strain306 infection on *citrus* leaves. (A) D-leucine and IAN reduced canker symptom development on grapefruit leaves spray-inoculated by strain 306 (approximately $10^8$ CFU/mL). Images are representative of four independent replicates at 28 days post inoculation. Xac306: strain 306 alone; D-leu/Xac306: D-leucine (10 mM) inoculated simultaneously with strain 306; IAN/Xac306: 3-indolylacetonitrile (100 μg/mL) inoculated simultaneously with strain 306; D-leu/Xac306 (6 h L): D-leucine (10 mM) inoculated 6 h before strain 306; IAN/Xac306 (6 h L): 3-indolylacetonitrile (100 μg/mL) inoculated 6 h before strain 306; $H_2O$: water only; Cu/Xac306: $CuSO_4$ (100 μg/mL) inoculated simultaneously with strain 306; D-leu/Cu/Xac306: D-leucine (10 mM) and $CuSO_4$ (100 μg/mL) inoculated simultaneously with strain 306; IAN/Cu/Xac306: 3-indolylacetonitrile (100 μg/mL) and $CuSO_4$ (100 μg/mL) inoculated simultaneously with strain 306; D-leu/IAN/Cu/Xac306: D-leucine (10 mM), 3-indolylacetonitrile (100 μg/mL) and $CuSO_4$ (100 μg/mL) inoculated simultaneously with strain 306; Xac306/D-leu (6 h L): D-leucine (10 mM) inoculated 6 h after strain 306; Xac306/IAN (6 h L): 3-indolylacetonitrile (100 μg/mL) inoculated 6 h after strain 306. (B) D-leucine and IAN affected the growth of strain 306 populations on grapefruit leaves following spray inoculation ($10^8$ CFU/mL). Bacterial cells were extracted from the leaves at different time points after inoculation and quantified using the standard serial diluting-plating method. The values shown are means of three repeats and standard deviations. All the assays were repeated three times with similar results.
Figure 5:
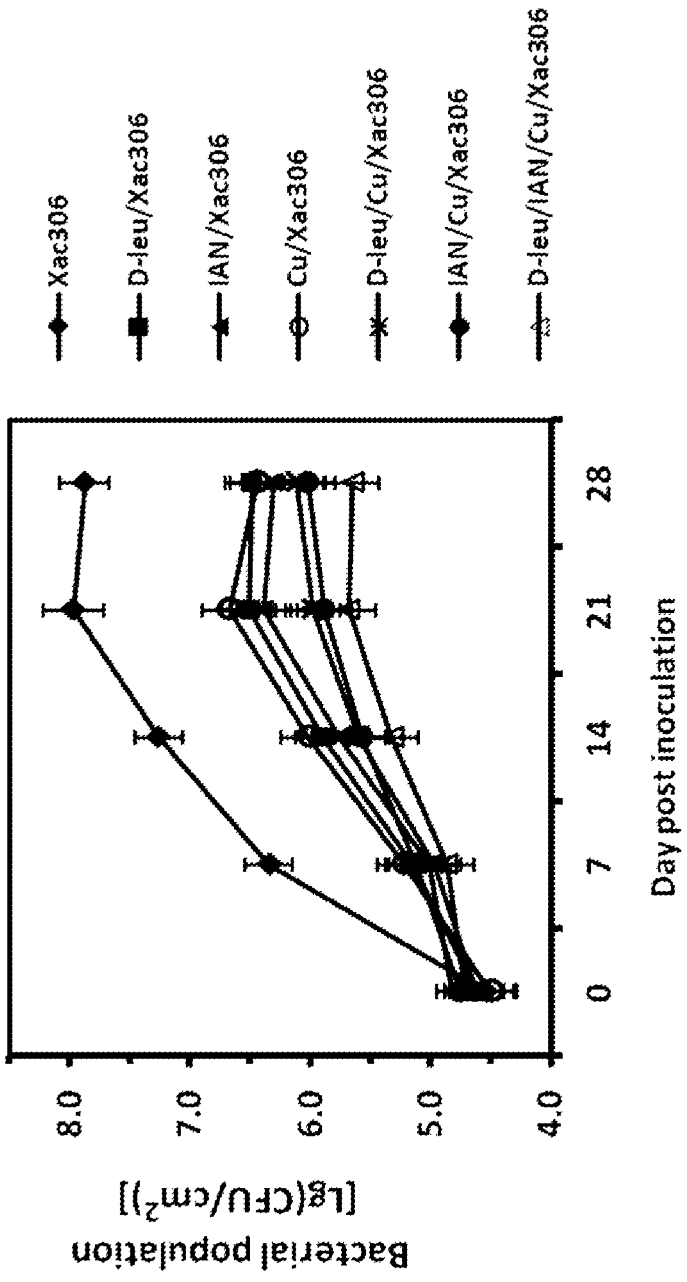

D-Leucine and IAN Reduce Canker Symptom Production and Bacterial Populations in Planta Plant inoculation by spray showed that both D-leucine (10 mM) and IAN (100 μg/mL) were able to reduce canker symptom development on grapefruit leaves when applied along with or prior to the pathogen inoculation, as evidenced by decreased lesion numbers compared to the positive control (pathogen inoculation alone) (FIG. 5A). Differences in lesion numbers were notable by 14 dpi and more distinctive over the remainder of the experiment. When applied after the pathogen inoculation, either D-leucine or IAN did not affect the development of canker symptoms (FIG. 5 A). Both D-leucine and IAN could reduce the level of canker lesions to that of copper spray ($CuSO_4$, 100 μg/mL). The leaves sprayed with D-leucine (10 mM), IAN (100 μg/mL) or $CuSO_4$ (100 μg/mL) displayed a similar level of canker lesions, less than that sprayed with the pathogen alone (FIG. 5 A). The combination of D-leucine (10 mM), IAN (100 μg/mL) and $CuSO_4$ (100 μg/mL) were more effective in suppressing the development of canker symptoms than $CuSO_4$ alone, with less lesions produced on the leaves (FIG. 5 A). These visual observations correlated with bacterial populations recovered from the inoculated leaves after inoculation that revealed an approximately 10 to 100-fold decrease in CFU/$mm^2$ leaf tissue for treatment with D-leucine, IAN, or $CuSO_4$, alone or in combination, compared to the untreated control (FIG. 5 B). Treatment of the grapefruit leaves with D-leucine, IAN or $CuSO_4$ alone resulted in an approximate 1.0 log reduction in the number of CFU compared to the untreated control, while treatment with a combination of D-leucine or/and IAN and $CuSO_4$ resulted in an approximate 2.0 log reduction in the number of CFU compared to the untreated control during 7 to 28 days after inoculation (FIG. 5 B).

Preliminary Study Showed that Both D-Leucine and IAN could Reduce Canker Symptom Production and *X. citri* Subsp, *Citri* Populations on *Citrus* Fruit at a Concentration Lower than the MIC.

Figure 6:
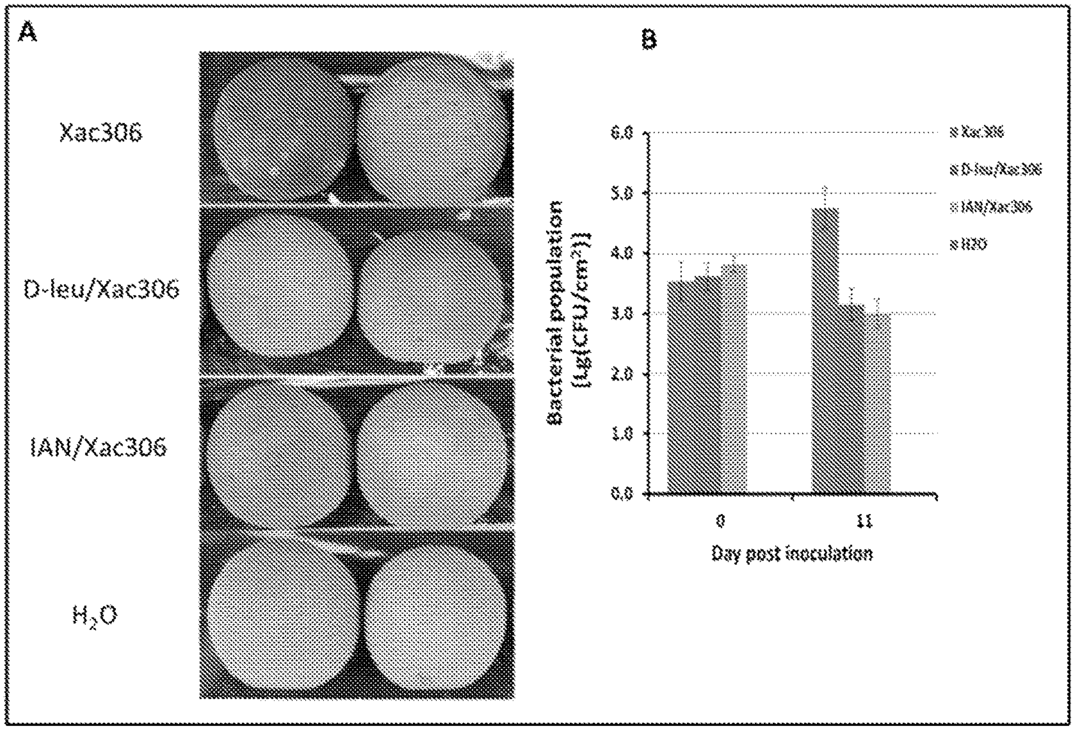
FIG. 6. Effect of D-leucine and 3-indolylacetonitrile (IAN) on *Xanthomonas citri* subsp. *citri* strain 306 infection on *citrus* fruit. A, D-leucine and IAN reduced canker symptom development on grapefruit fruit spray-inoculated by Xac 306 (approximately $10^8$ CFU/ml). Images are representative of six independent replicates at 10 days postinoculation. Xac 306: strain 306 alone (positive control); D-leu/Xac306: D-leucine (10 mM) inoculated simultaneously with Xac 306; IAN/Xac306: 3-indolylacetonitrile (100 μg/ml) inoculated simultaneously with Xac 306; $H_2O$: water only (negative control); B, D-leucine and IAN affected the growth of Xac 306 populations on grapefruit fruit following spray inoculation ($10^8$ CFU/ml). Bacterial cells were extracted from the fruit surface at different time points after inoculation and quantified using the standard serial diluting-plating method. The values shown are means of three repeats and standard deviations.

Detached immature *citrus* fruit (grapefruit, 20-40 mm in diameter) inoculation by spraying *X. citri* subsp. *citri* ($10^8$ CFU/ml) showed that both D-leucine (10 mM) and IAN (100 μg/ml) were able to reduce canker symptom development on fruit surface when applied along with the pathogen inoculation, as evidenced by decreased lesion numbers compared with the positive control (pathogen inoculation alone) (FIG. 6A). The visual observations correlated with bacterial populations recovered from the surface of inoculated fruit that revealed an approximately 50-fold decrease in CFU per square centimeter of fruit tissue for treatment with D-leucine or IAN, compared with the untreated control (FIG. 6B). Treatment of the fruit with D-leucine and IAN resulted in an approximate 1.6 and 1.8 log reduction in the number of CFU per square centimeter respectively, compared with the untreated control at 11 days after inoculation (FIG. 6B).

C. Discussion

In the above examples, it was demonstrated that D-leucine and IAN reduced biofilm formation by Xac and increased the susceptibility to copper at a concentration without affecting its growth. Canker control activity was evaluated as the ability to reduce the number of lesions and populations of Xac on *citrus* leaves after applications. The results of this greenhouse assays support the use of foliar-applied biofilm inhibitors alone or combined with copper-based bactericides for the control of canker disease on *citrus* trees.

D-leucine and IAN appear to have distinct mechanisms of action in reducing biofilm formation by Xac. In this study, it was found that both D-leucine and IAN inhibit the biofilm formation of Xac on different abiotic surfaces and host leaves at sub-MIC concentrations (FIG. 2), while only IAN repressed expression of several biofilm formation related genes (chemotaxis/motility-related genes) in Xac (FIG. 3). Flagellar-mediated chemotaxis/motility and type IV pili protein are necessary for Xac biofilm formation (Li and Wang, 2011). The observation of IAN repressed expression of genes related to bacterial motility was consistent with previous reports for IAN effect on biofilm formation in the human bacterial pathogen *Pseudomonas aeruginosa* (Lee et al., 2011). Hence, IAN probably reduces Xac biofilm formation by repressing these chemotaxis/motility-related genes (cheY, motB and pilB) (FIG. 3) and thus reducing its chemotaxis and motility. Interestingly, it has been found that several D-amino acids including D-leucine inhibit biofilm formation in *Bacillus subtilis* and *Staphylococcus aureus* by preventing protein localization at the cell surface (Hochbaum et al., 2011). Whether D-leucine prevents protein localization at the cell surface of Xac remains unknown.

Reduced sensitivity to copper in bacteria may result from genetic mutations and from the change of environmental factors influencing the ionic concentration or production of bacterial extracellular polysaccharides (EPS) that can bind the biologically active ions of copper (Hasman et al., 2009; Hsiao et al., 2011). It has also been shown that decreased sensitivity of bacteria to copper can be mediated by biofilms (Rodrigues et al., 2008). In the experimental conditions described herein, the results showed that both D-leucine and IAN increased the susceptibility of Xac planktonic and biofilm cells to copper (FIG. 4), but did not affect expression of genes responsible for gum EPS biosynthesis or related to copper resistance (data not shown). It is possible that D-leucine and IAN may be affecting Xac resistance by suppressing biofilm formation or causing bacteria to remain in a planktonic state making them more sensitive to copper.

Preventive effects of D-leucine and IAN have been demonstrated on Xac-spray inoculated *citrus* young plants by foliar spraying. In greenhouse assays, foliar spray applications of D-leucine and IAN, 6 hours pre-inoculation or co-inoculation, reduced the number of lesions produced by Xac and the bacterial populations on grapefruit leaves (FIG. 5). The data obtained suggested that D-leucine and IAN suppressed or possibly dispersed biofilms of Xac on host plant surfaces, which may cause impaired infection. Furthermore, the combined application of D-leucine, IAN, and copper enhanced activities against the Xac bacterium compared with the application of copper alone, demonstrating an apparent synergetic effect that will permit a dosage reduction of copper. It would be of great value to decrease the copper usage in the open environment as it reduces the potential for side effects to the environment.

REFERENCES

Alva, A. K. 1993. Copper contamination of sandy soils and effects on young Hamlin orange trees. Bull. Environ. Contam, Toxicol. 51:857-864.

Behlau, F., Belasque, J., Jr., Graham, J. H., and Leite, R. P., Jr, 2010. Effect of frequency of copper applications on control of *citrus* canker and the yield of young bearing sweet orange trees. Crop Prot. 29, 300-305.

Behlau, F., Canteros, B. I., Jones, J. B., and Graham, J. H. 2012. Copper resistance genes from different xanthomonads and *citrus* epiphytic bacteria confer resistance to *Xanthomonas citri* subsp. *citri*. Eur. J Plant Pathol. 133:949-963.

Brunings, A., and Gabriel, D. 2003. *Xanthomonas citri*: breaking the surface. Mol. Plant Pathol, 4: 141-157.

da Silva, A. C., Ferro, J. A., Reinach, F. C., Farah, C. S., Furlan, L. R., Quaggio, R. B., Monteiro-Vitorello, C. B., Van Sluys, M. A., Almeida, N. F., Alves, L. M., do Amaral, A. M., Bertolini, M. C., Camargo, L. E., Camarotte, G., Cannavan, F., Cardozo, J., Chambergo, F., Ciapina, L. P., Cicarelli, R. M., Coutinho, L. L., Cursino-Santos, J. R., El-Dorry, H., Faria, J. B., Ferreira, A. J., Ferreira, R. C., Ferro, M. I., Formighieri, E. F., Franco, M. C., Greggio, C. C., Gruber, A., Katsuyama, A. M., Kishi, L. T., Leite, R. P., Lemos, E. G., Lemos, M. V., Locali, E. C., Machado, M. A., Madeira, A. M., Martinez-Rossi, N. M., Martins, E. C., Meidanis, J., Menck, C. F., Miyaki, C. Y., Moon, D. H., Moreira, L. M., Novo, M. T., Okura, V. K., Oliveira, M. C., Oliveira, V. R., Pereira, H. A., Rossi, A., Sena, J. A., Silva, C., de Souza, R. F., Spinola, L. A., Takita, M. A., Tamura, R. E., Teixeira, E. C., Tezza, R. L, Trindade dos Santos, M., Truffi, D., Tsai, S. M., White, F. F., Setubal, J. C. and Kitajima, J. P. 2002. Comparison of the genomes of two *Xanthomonas* pathogens with differing host specificities. Nature 417:459-463.

Gottig, N., Garavaglia, B. S., Garofalo, C. G., Orellano, E. G. and Ottado, J. 2009. A filamentous hemagglutinin-like protein of *Xanthomonas axonopodis* pv. *citri*, the phytopathogen responsible for *citrus* canker, is involved in bacterial virulence. PLoS ONE 4:e4358.

Gottwald, T. R., and Irey, M. 2007. Post-hurricane analysis of *citrus* canker II: predictive model estimation of disease spread and area potentially impacted by various eradication protocols following catastrophic weather events. Plant Health Prog. Online. doi:10.1094/PHP-2007-0405-01-RS.

Gottwald, T. R., Graham, J. H. and Schubert, T. S. 2002. *Citrus* canker: the pathogen and its impact. Plant Health Prog. Online. doi:10.1094/PHP-2002-0812-01-RV.

Gottwald, T. R., Graham, J. H., Bock, C., Bonn, G., Civerolo, E., Irey, M., Leite, R., McCollum, G., Parker, P., Ramallo, J., Riley, T., Schubert, T., Stein, B., and Taylor, E. 2009. The epidemiological significance of post-packinghouse survival of *Xanthomonas citri* subsp. *citri* for dissemination of Asiatic *citrus* canker via infected fruit. Crop Prot. 28:508-524.

Graham, J. H., Dewdney, M. M., and Myers, M. E. 2010. Streptomycin and copper formulations for control of *citrus* canker on grapefruit. Proceedings of the Florida State Horticultural Society 123:92-98.

Graham, J. H., Gottwald, T. R., Cubero, J. and Achor, D. S. 2004. *Xanthomonas axonopodis* pv. *citri*: factors affecting successful eradication of *citrus* canker. Mol. Plant Pathol. 5:1-15, Guo, Y., Sagaram, U. S., Kim, J. S., and Wang, N. 2010. Requirement of the galU gene for polysaccharide production by and pathogenicity and growth in planta of *Xanthomonas citri* subsp. *citri*. Appl. Environ. Microbiol. 76:2234-2242, Hasman, H., Bjerrum, M. J., Christiansen, L. E., Hasen, H. C. B., and Aarestrup, F. M. 2009. The effect of pH and storage on copper speciation and bacterial growth in complex media. J. Microbiol. Method. 78:20-24.

Hochbaum, A. I., Kolodkin-Gal, I., Foulston, L., Kolter, R., Aizenberg, J., and Losick, R. 2011. Inhibitory effects of D-amino acids on *Staphylococcus aureus* biofilm development. J. Bacterial. 193:5616-5622.

Hsiao, Y., Liu, Y., Lee, P., Hsu, P., Tseng, S., and Pan, Y. 2011. Functional characterization of copA gene encoding multicopper oxidase in *Xanthomonas campestris* pv. *campestris*, J. Agric. Food Chem. 59:9290-9302.

Irey, M. S., Gottwald, T. R., Graham, J., Riley, T., and Carlton, G. 2006. Post-hurricane analysis of *citrus* canker spread and progress towards the development of a predictive model for future weather related spread. Plant Health Prog. Online. doi:10.1094/PHP-2006-0822-01-RS.

Kolodkin-Gal, I., Romero, D., Cao, S., Clardy, J., Kolter, R., and Losick, R. 2010. D-amino acids trigger biofilm disassembly. Science 328:627-629.

Laia, M., Moreira, L., Dezajacomo, J., Brigati, J., Ferreira, C., Ferro, M., Silva, A., Ferro, J., and Oliveira, J. 2009. New genes of *Xanthomonas citri* subsp. *citri* involved in pathogenesis and adaptation revealed by a transposon-based mutant library. BMC Microbiol. 9:12.

Lee, J. H., Cho, M. H., and Lee, J. 2011. 3-Indolylacetonitrile decreases *Escherichia coli O*157:H7 biofilm formation and *Pseudomonas aeruginosa* virulence. Environ. Microbiol. 13:62-73.

Li, J., and Wang, N. 2011. Genome-wide mutagenesis of *Xanthomonas axonopodis* pv. *citri* reveals novel genetic determinants and regulation mechanisms of biofilm formation. PLoS ONE 6:e21804.

Li, J., and Wang, N. 2012. The gpsX gene encoding a glycosyltransferase is important for polysaccharide production and required for full virulence in *Xanthomonas citri* subsp. *citri*. BMC Microbiol, 12:31.

Livak, K., and Schmittgen, T. 2001. Analysis of relative gene expression data using real-time quantitative PCR and the 2-DeltaDeltaCT method. Methods 25:402-408.

Rigano, L. A., Siciliano, F., Enrique, R., Sendin, L., Filippone, P., Torres, P. S., Questa, J., Dow, J. M., Castagnaro, A. P., Vojnov, A. A. and Marano, M. R. 2007. Biofilm formation, epiphytic fitness, and canker development in *Xanthomonas axonopodis* pv. *citri*. Mol. Plant-Microbe Interact. 20:1222-1230.

Ritchie, D. F., and Dittapongpitch, V. 1991. Copper- and streptomycinresistant strains and host differentiated races of *Xanthomonas campestris* pv. *vesicatoria* in North Carolina. Plant Dis. 75:733-736.

Rodrigues, C. M., Takita, M. A., Coletta-Filho, H. D., Olivato, J. C., Caserta, R., Machado, M. A., and de Souza, A. A. 2008. Copper resistance of biofilm cells of the plant pathogen *Xylella fastidiosa*. Appl. Microbiol. Biotechnol. 77:1145-1157.

Romero, D., Vlamakis, H. Losick, R., and Kolter, R. 2011. An accessory protein required for anchoring and assembly of amyloid fibers in *B. subtilis* biofilms. Mol. Microbiol. 80:1155-1168.

Rybak, M., Minsavage, G. V., Stall, E. and Jones, J. B. 2009. Identification of *Xanthomonas citri* subsp. *citri* host specificity genes in a heterologous expression host. Mol. Plant Pathol. 10:249-262.

Schaad, N., Postnikova, E., Lacy, G., Sechler, A., Agarkova, I., Stromberg, P., Stromberg, V., and Vidaver, A. 2006. Emended classification of xanthomonad pathogens on *citrus*. Syst. Appl. Microbiol. 29:690-695.

Shiotani, H., Uematsu, H., Tsukamoto, T., Shimizu, Y., Ueda, K., Mizuno, A., and Sato, S. 2009. Survival and dispersal of *Xanthomonas citri* pv. *citri* from infected Satsuma mandarin fruit. Crop Prot. 28:19-23.

Teixeira, E. C., Franco de Oliveira, J. C., Marques Novo, M. T. and Bertolini, M. C. 2008. The copper resistance operon copAB from *Xanthomonas axonopodis* pathovar *citri*: gene inactivation results in copper sensitivity. Microbiology 154:402-412.

Teitzel, G. M., and Parsek, M. R. 2003. Heavy metal resistance of biofilm and planktonic *Pseudomonas aeruginosa*. Appl. Environ. Microbiol. 69:2313-2320.

Yan, Q., and Wang, N. 2011. The ColR/ColS two-component system plays multiple roles in the pathogenicity of the *citrus* canker pathogen *Xanthomonas citri* subsp. *citri*. J. Bacteriol. 193:1590-1599.

Yan, Q., and Wang, N. 2012. High-throughput screening and analysis of genes of *Xanthomonas citri* subsp. *citri* involved in *citrus* canker symptom development. Mol. Plant-Microbe Interact. 25: 69-84.

It should be borne in mind that all patents, patent applications, patent publications, technical publications, scientific publications, and other references referenced herein and in the accompanying appendices are hereby incorporated by reference in this application to the extent not inconsistent with the teachings herein.

It is important to an understanding to note that all technical and scientific terms used herein, unless defined herein, are intended to have the same meaning as commonly understood by one of ordinary skill in the art. The techniques employed herein are also those that are known to one of ordinary skill in the art, unless stated otherwise. For purposes of more clearly facilitating an understanding the invention as disclosed and claimed herein, the following definitions are provided.

While a number of embodiments have been shown and described herein in the present context, such embodiments are provided by way of example only, and not of limitation. Numerous variations, changes and substitutions will occur to those of skilled in the art without materially departing from the invention herein. For example, the present invention need not be limited to best mode disclosed herein, since other applications can equally benefit from the teachings. Also, in the claims, means-plus-function and step-plus-function clauses are intended to cover the structures and acts, respectively, described herein as performing the recited function and not only structural equivalents or act equivalents, but also equivalent structures or equivalent acts, respectively. Accordingly, all such modifications are intended to be included within the scope of this invention as defined in the following claims, in accordance with relevant law as to their interpretation.

TABLE 1

Genes and corresponding primers used in quantitative real-time reverse transcription polymerase chain reaction (qRT-PCR)

| Gene | Locus_tag | Function of protein product | Primer Sequence (5'-3') |
|---|---|---|---|
| gumB | XAC2585 | EPS xanthan biosynthesis | Forward: agaacggccatatttcgttg<br>Reverse: tgcagataaccgttgcgata |
| gumD | XAC2583 | EPS xanthan biosynthesis | Forward: tccgtaccccatacgacatt<br>Reverse: taccagcttgacgttgatcg |

TABLE 1-continued

Genes and corresponding primers used in quantitative real-time reverse transcription polymerase chain reaction (qRT-PCR)

| Gene | Locus_tag | Function of protein product | Primer Sequence (5'-3') |
|---|---|---|---|
| galU | XAC2292 | Polysacchrides biosythesis | Forward: acagtgccgaaagaaatgct Reverse: agctcataggccttgtcgaa |
| rfbC | XAC3598 | LPS 0-antigen biosynthesis | Forward: atcatcccggtctgcaatac Reverse: ggaatgcgcttcttgaactc |
| cheA | XAC1930 | Chemotaxis protein | Forward: gacgatattgctgccgattt Reverse: gagctggtcggcttcttct |
| cheY | XAC1904 | Bacterial chemotaxis regulator | Forward: tacaagttcacccccatgct Reverse: gcgatcagctgttctggatt |
| mcpA | XAC1746 | Chemotaxis protein | Forward: cctatcgaacctgcttggac Reverse: cacctcgtccagtcgatacc |
| motB | XAC1908 | Flagellar motor protein | Forward: atctgtggatcgaggtggag Reverse: gttcccagttggagggaaat |
| fleN | XAC1934 | Flagellar biosynthesis | Forward: agtctcgttcttcgccttga Reverse: gttggtcagcttggcgtatt |
| fliC | XAC1975 | Flagellar biosynthesis | Forward: cagcgtattcgtgagctgtc Reverse: ccgttgaagttggtctggtt |
| pilB | XAC3239 | Pilus biogenesis | Forward: caagtgctaccgctgttcaa Reverse: gcgacggatctgatcttcat |
| Clp | XAC0483 | cAMP regulatory protein | Forward: gaactaccatgagcccagga Reverse: gccgctgatcacgtagtaga |
| colR | XAC3250 | Response regulator | Forward: ttggcgattacctcgaagac Reverse: gttgaggtcgagcacgatg |
| rpfG | XAC1877 | Response regulator | Forward: ggatctgggattgaacatcg Reverse: agtccagcaacagcagatcc |
| rpoN | XAC1969 | RNA polymerase sigma-54 factor | Forward: gcttccatgaagacgaccat Reverse: gctcttccaactccagcaac |
| copA | XAC3630 | Copper resistance protein | Forward: cgatgtttcaggagcagtca Reverse: tgtttcaaacgacggaacag |
| copB | XAC3631 | Copper resistance protein | Forward: ctcaccgagacacgcactaa Reverse: ccgatcgagcaggacataat |
| gyrA | XAC1631 | DNA gyrase subunit A | Forward: cgtcacgttgatccgttgt Reverse: gcttgcttggtccactccct |

TABLE 2

Minimum inhibitory concentrations (MICs) of copper ($CuSO_4$) against *X. citri* subsp. *citri* strain 306 in NB medium with or without biofilm inhibitor*

| Treatment | MIC (mM) |
|---|---|
| $CuSO_4$ | 0.5 |
| D-leucine | 16.0 |
| D-serine | 8.0 |
| IAN | 200 (μg/mL) |
| $CuSO_4$/D-leucine (10 mM) | 0.25 |
| $CuSO_4$/IAN (100 μg/ml) | 0.25 |
| $CuSO_4$/D-leucine (10 mM)/IAN (100 μg/ml) | 0.25 |

*The MICs were examined using a 96-well plate assay at 28° C. under stationary conditions as described in the Materials and Methods. The MIC was defined as the lowest concentration resulting in no bacterial growth measured at $OD_{600}$ after a 48 h-incubation, compared to the control samples. The determinations were repeated three times with eight replicate wells each time.

LEUCINE DERIVATIVES

| Product # | Image | Description | Molecular Formula |
|---|---|---|---|
| 482609 | 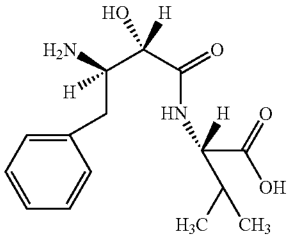 [SMILES: CC(C)[C@H](NC(=O)[C@@H](O)[C@H](N)Cc1ccccc1)C(=O)O] | N[(2S,3R)-3-Amino-2-hydroxy-4-phenylbutyryl]-L-leucine 97% | $C_{16}H_{24}N_2O_4$ |
| 11578 | 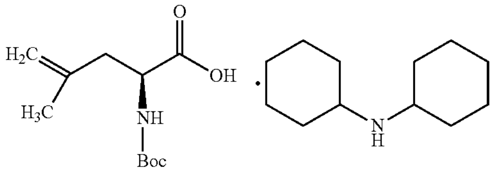 | Boc-4,5-dehydro-Leu-OH (dicyclohexylammonium) salt ≥96.0% (HPLC) | $C_{11}H_{19}NO_4 \cdot C_{12}H_{23}N$ |
| 15442 | 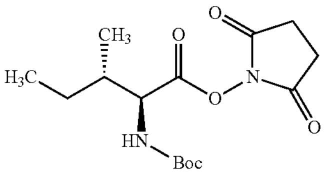 [SMILES: CC[C@H](C)[C@H](NC(=O)OC(C)(C)C)C(=O)ON1C(=O)CCC1=O] | Boc-Ile-OSu ≥98.0% (HPLC) | $C_{15}H_{24}N_2O_6$ |
| A48105 | 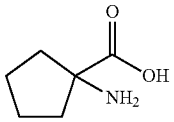 | Cycloleucine 97% | $C_6H_{11}NO_2$ |
| 251526 | 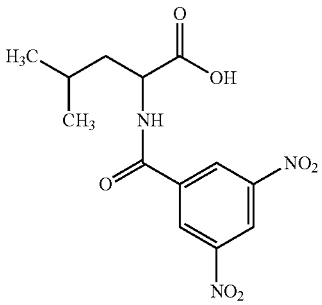 [SMILES: CC(C)CC(NC(=O)c1cc([N+](=O)[O-])cc([N+](=O)[O-])c1)C(=O)O] | N-(3,5-Dinitrobenzoyl)-DL-leucine 99% | $C_{13}H_{15}N_3O_7$ |
| 47524 | 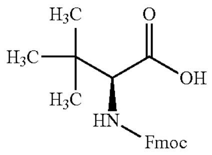 | Fmoc-tBu-Gly-OH ≥98.0% | $C_{21}H_{23}NO_4$ |

-continued
LEUCINE DERIVATIVES
| Product # | Image | Description | Molecular Formula |
|---|---|---|---|
| 759945 | 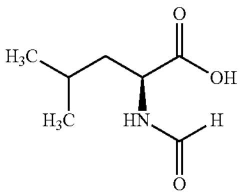 | N-Formyl-Leu-OH 90% | $C_7H_{13}NO_3$ |
| 347914 | 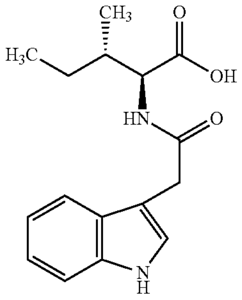 [SMILES: CC[C@H](C)[C@H](NC(=O)Cc1c[nH]c2ccccc12)C(=O)O] | N-(3-Indolylacetyl)-L-isoleucine 99% | $C_{16}H_{20}N_2O_3$ |
| 61835 | 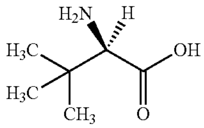 | D-tert-Leucine puriss., ≥99.0% (NT) | $C_6H_{13}NO_2$ |
| 269115 | 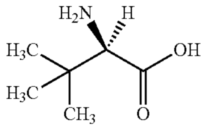 | D-tert-Leucine 98% | $C_6H_{13}NO_2$ |
| 61825 | 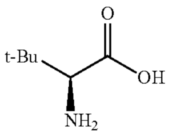 | L-tert-Leucine puriss., ≥99.0% (NT) | $C_6H_{13}NO_2$ |
| 269107 | 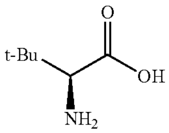 | L-tert-Leucine 99% | $C_6H_{13}NO_2$ |
| 61837 | 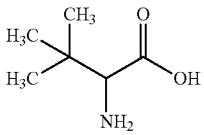 | DL-tert-Leucine puriss., ≥99.0% (NT) | $C_6H_{13}NO_2$ |
| 332178 | 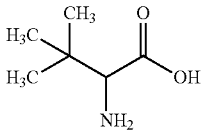 | DL-tert-Leucine 98% | $C_6H_{13}NO_2$ |

-continued

LEUCINE DERIVATIVES

| Product # | Image | Description | Molecular Formula |
| --- | --- | --- | --- |
| 61891 | 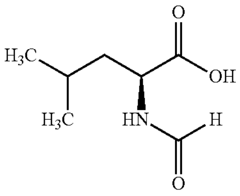 | L-tert-Leucine methyl ester hydrochloride ≥99.0% (AT) | $C_7H_{15}NO_2$•HCl |
| 91917 | 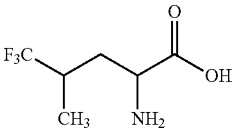 | 5,5,5-Trifluoro-DL-leucine ≥98.0% (sum of isomers. HPLC) | $C_6H_{10}F_3NO_2$ |

See more at: http://www.sigmaaldrich.com/chemistry/chemistry-products.html?TablePage=16276130#sthash.kC33FwiT.dpuf

SERINE DERIVATIVES

| Product # | Image | Description | Molecular Formula |
| --- | --- | --- | --- |
| 712779 | 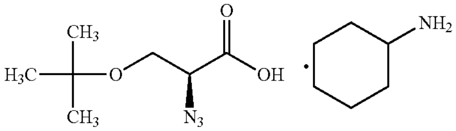 | (S)-2-Azido-3-tert-butoxypropionic acid cyclohexylammonium salt ≥98% (TLC) | C7$H_{13}N_3O_3$•$C_6H_{13}N$ |
| 13910 | 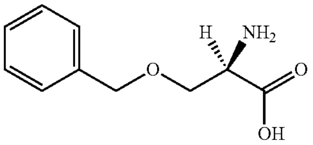 [SMILES: N[C@H](COCc1ccccc1)C(=O)O] | O-Benzyl-D-serine ≥0.99.0% | $C_{10}H_{13}NO_3$ |
| 13900 | 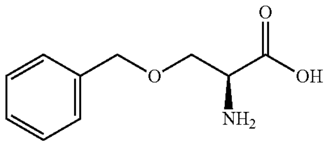 [SMILES: N[C@@H](COCc1ccccc1)C(=O)O] | O-Benzyl-L-serine ≥99.0% (NT) | $C_{10}H_{13}NO_3$ |
| 13920 | 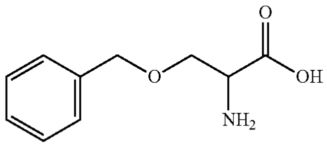 [SMILES: NC(COCc1ccccc1)C(=O)O] | O-Benzyl-DL-serine ≥99.0% | $C_{10}H_{13}NO_3$ |
| CDS006888 | 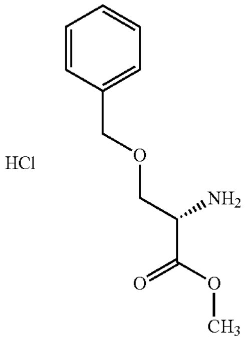 | o-Benzyl-L-serine methyl ester hydrochloride Aldrich$^{CPR}$ | $C_{11}H_{16}ClNO_3$ |

-continued
| SERINE DERIVATIVES | | | |
|---|---|---|---|
| Product # | Image | Description | Molecular Formula |
| 95029 | 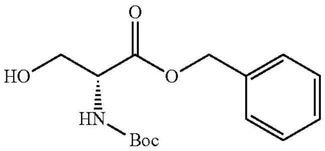 [SMILES: CC(C)(C)OC(=O)N[C@H](CO)C(=O)OCc1ccccc1] | Boc-D-Ser-O-Bzl ≥95.0% (HPLC) | $C_{15}H_{21}NO_6$ |
| 15390 | 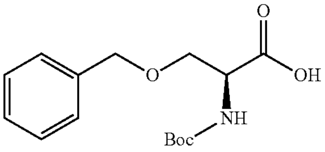 [SMILES: CC(C)(C)OC(=O)N[C@@H](COCc1ccccc1)C(=O)O] | Boc-Ser(Bzl)-OH ≥99.0% (T) | $C_{15}H_{21}NO_5$ |
| 15078 | 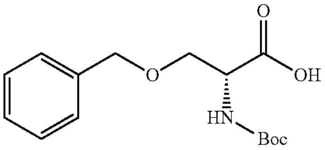 [SMILES: CC(C)(C)OC(=O)N[C@H](COCc1ccccc1)C(=O)O] | Boc-D-Ser(Bzl)-OH ≥98.0% (HPLC) | $C_{15}H_{21}NO_5$ |
| 15079 | 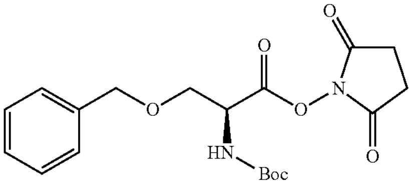 [SMILES: CC(C)(C)OC(=O)N[C@@H](COCc1ccccc1)C(=O)ON1C(=O)CCC1=O] | Boc-Ser(Bzl)-OSu ≥97.0% (HPLC) | $C_{19}H_{24}N_2O_7$ |
| 713473 | 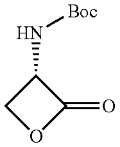 [SMILES: CC(C)(C)OC(=O)N[C@H]1COC1=O] | N-Boc-L-serine β-lactone ≥96.0% (GC) | $C_6H_{13}NO_4$ |
| 16726 | 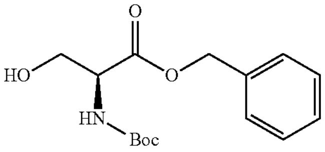 [SMILES: CC(C)(C)OC(=O)N[C@@H](CO)C(=O)OCc1ccccc1] | Boc-Ser-OBzl ≥95.0% | $C_{15}H_{21}NO_5$ |
| 15500 | 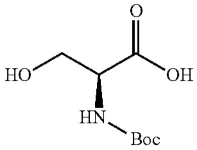 [SMILES: CC(C)(C)OC(=O)N[C@@H](CO)C(=O)O] | Boc-Ser-OH ≥99.0% (T) | $C_8H_{15}NO_5$ |
| 15182 | 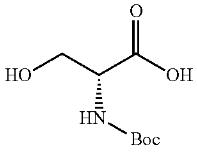 [SMILES: CC(C)(C)OC(=O)N[C@H](CO)C(=O)O] | Boc-D-Ser-OH ≥98.0% (TLC) | $C_8H_{15}NO_5$ |
| 410489 | 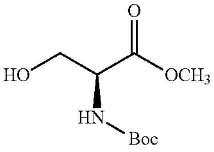 [SMILES: COC(=O)[C@H](CO)NC(=O)OC(C)(C)C] | Boc-Ser-OMe 95% | $C_9H_{17}NO_5$ |

-continued

| SERINE DERIVATIVES | | | |
|---|---|---|---|
| Product # | Image | Description | Molecular Formula |
| 03581 | 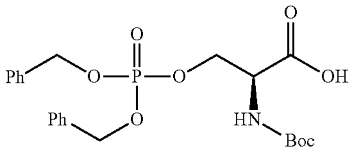 [SMILES: CC(C)(C)OC(=O)N[C@@H](COP(=O)(OCc1ccccc1)OCc1ccccc1)C(=O)O] | Boc-Ser($PO_3Bzl_2$)-OH ≥96.0% (TLC) | $C_{22}H_{28}NO_8P$ |
| 15432 | 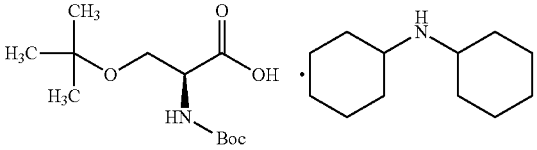 | BoC-Ser(tBu)-OH (dicyclohexylammonium) salt 99.0% (N) | $C_{12}H_{23}NO_5$•$C_{12}H_{23}N$ |
| 95028 | 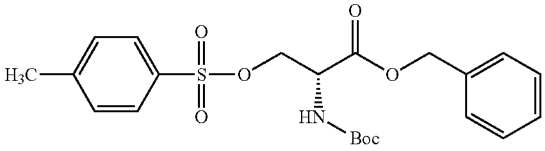 [SMILES: Cc1ccc(S(=O)(=O)OC[C@@H](NC(=O)OC(C)(C)C)C(=O)OCc2ccccc2)cc1] | Boc-D-Ser(Tos)-O-Bzl ≥97.0% | $C_{22}H_{27}NO_7S$ |
| 446068 | 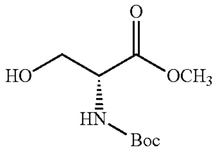 [SMILES: COC(=O)[C@@H](CO)NC(=O)OC(C)(C)C] | N-(tert-Butoxycarbonyl)-D-serine methyl ester 97% | $C_9H_{17}NO_5$ |
| B6278 | 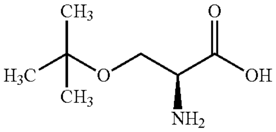 | O-tert-Butyl-L-serine | $C_7H_{15}NO_3$ |
| 20587 | 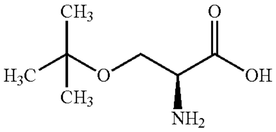 | O-tert-Butyl-L-serine purum, ≥97.0% (T) | $C_7H_{15}NO_3$ |
| 29589 | 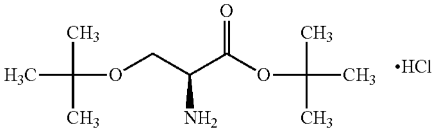 | O-tert-Butyl-L-serine tert-butyl ester hydrochloride ≥98.0 (AT) | $C_{11}H_{23}NO_3$•HCl |
| 78994 | 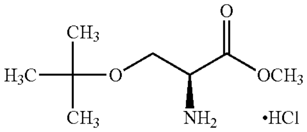 | O-tert-Butyl-L-serine methyl ester hydrochloride ≥98.0% (TLC) | $C_8H_{17}NO_3$•HCl |
| 53953 | 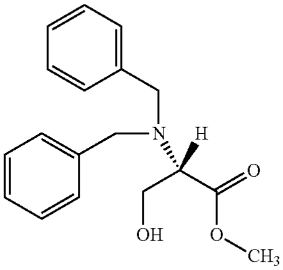 [SMILES: COC(=O)[C@H](CO)N(Cc1ccccc1)Cc1ccccc1] | N,N-Dibenzyl-L-serine methyl ester 97% | $C_{18}H_{21}NO_3$ |

-continued
| SERINE DERIVATIVES | | | |
|---|---|---|---|
| Product # | Image | Description | Molecular Formula |
| CDS019472 | 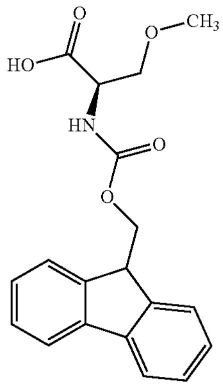 [SMILES: COC[C@@H](NC(=O)OCC1c2ccccc2-c2ccccc21)C(=O)O] | Fmoc-o-methyl-L-Ser Aldrich[CPR] | $C_{19}H_{19}NO_5$ |
| CDS019194 | 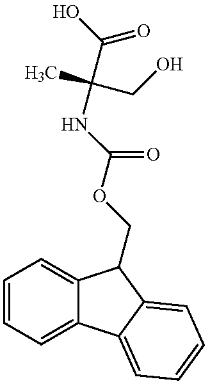 [SMILES: C[C@@](CO)(NC(=O)OCC1c2ccccc2-c2ccccc21)C(=O)O] | Fmoc-α-methyl-D-Ser Aldrich[CPR] | $C_{19}H_{19}NO_5$ |
| 47678 | 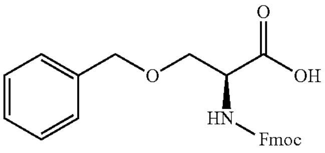 | Fmoc-Ser(Bzl)-OH ≥98.0% (HPLC) | $C_{25}H_{23}NO_5$ |
| CDS020076 | 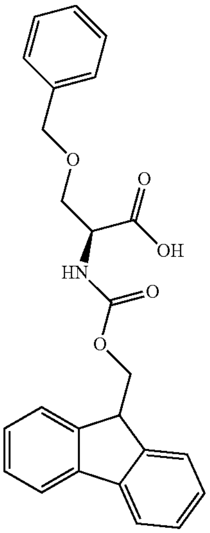 [SMILES: O=C(N[C@@H](COCc1ccccc1)C(=O)O)OCC1c2ccccc2-c2ccccc21] | Fmoc-D-Ser(Bzl)-OH Aldrich[CPR] | $C_{25}H_{23}NO_5$ |

-continued
| SERINE DERIVATIVES | | | |
|---|---|---|---|
| Product # | Image | Description | Molecular Formula |
| 47601 | 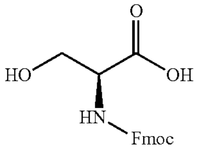 | Fmoc-Ser-OH ≥97.0% (sum of enantiomers, HPLC) | $C_{18}H_{17}NO_5$ |
| 47533 | 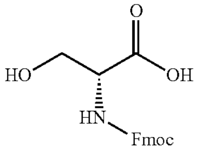 | Fmoc-D-Ser-OH ≥98.0% | $C_{18}H_{17}NO_5$ |
| 09769 | 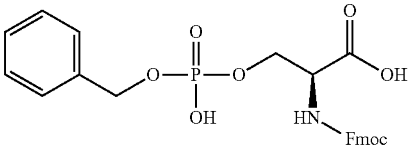 | Fmoc-Ser(PO3BzlH)-OH ≥97.0% (HPLC) | $C_{25}H_{24}NO_8P$ |
| 47619 | 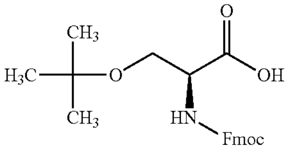 | Fmoc-Ser(tBu)-OH ≥98.0% (HPLC) | $C_{22}H_{25}NO_5$ |
| 47311 | 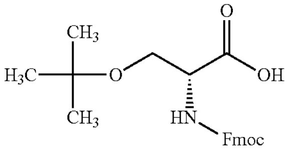 | Fmoc-D-Ser(tBu)-OH ≥98.0 (TLC) | $C_{22}H_{25}NO_5$ |
| 00231 | 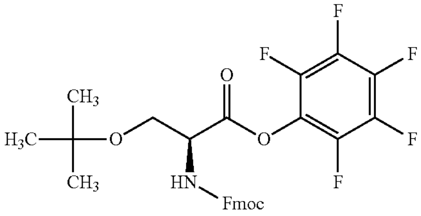 | Fmoc-Ser(tBu)-OPfp technical, ≥90% (HPLC) | $C_{28}H_{24}F_5NO_6$ |
| 47563 | 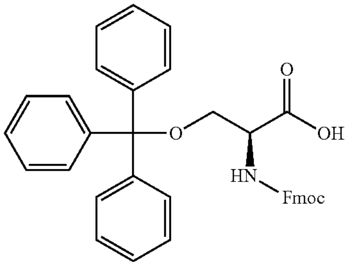 | Fmoc-Ser(Trt)-OH ≥98.0% | $C_{37}H_{31}NO_5$ |
| CDS006560 | 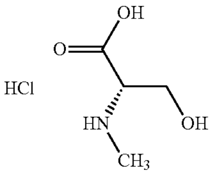 | H-L-Meser-OH hydrochloride Aldrich[CPR] | $C_4H_{10}ClNO_3$ |

-continued

| SERINE DERIVATIVES | | | |
|---|---|---|---|
| Product # | Image | Description | Molecular Formula |
| 375799 | 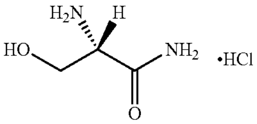 | L-Serinamide hydrochloride 98% | $C_3H_8N_2O_2$•HCl |
| S4250 | 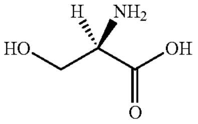 | D-Serine ≥90% (TLC) | $C_3H_7NO_3$ |
| S4500 | 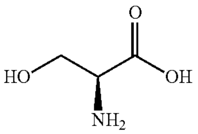 | L-Serine ReagentPlus ®, ≥99% (TLC) | $C_3H_7NO_3$ |
| S4311 | 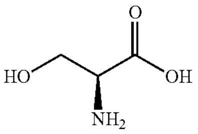 | L-Serine from non-animal source, meets EP, USP testing specifications, suitable for cell culture, 98.5-101.0% | $C_3H_7NO_3$ |
| 84960 | 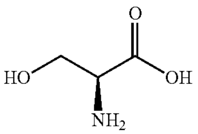 | L-Serine ≥99.0% (NT) | $C_3H_7NO_3$ |
| S4375 | 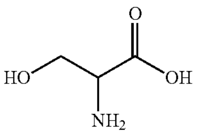 | DL-Serine ≥98% (TLC) | $C_3H_7NO_3$ |
| 78568 | 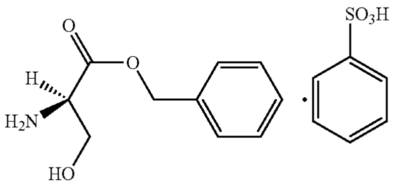 | D-Serine benzyl ester benzenesulfonate ≥98.0% (HPLC) | $C_{10}H_{13}NO_3$•$C_6H_8O_3S$ |
| 04934 | 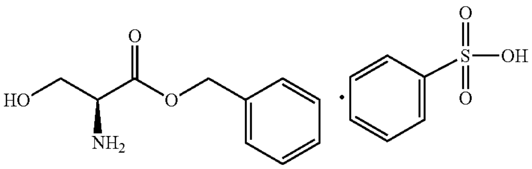 | L-Serine benzyl ester benzenesulfonate (salt) ≥98.0% (HPLC) | $C_{10}H_{13}NO_3$•$C_8H_6O_3S$ |
| 223123 | 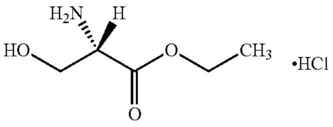 | L-Serine ethyl ester hydrochloride 99% (TLC) | $C_5H_{11}NO_3$•HCl |
| 84985 | 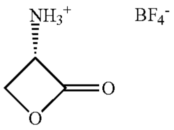 | L-Serine β-lactone tetrafluoroborate salt ≥98.0% (T) | $C_3H_8NO_2$•$BF_4$ |

-continued

| SERINE DERIVATIVES | | | |
|---|---|---|---|
| Product # | Image | Description | Molecular Formula |
| 445797 | 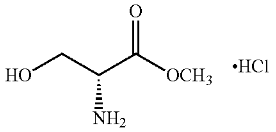 | D-Serine methyl ester hydrochloride 98% | $C_4H_9NO_3$•HCl |
| 85000 | 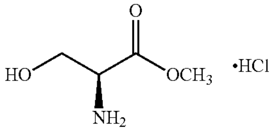 | L-Serine methyl ester hydrochloride purum, ≥99.0% (AT) | $C_4H_9NO_3$•HCl |
| 412201 | 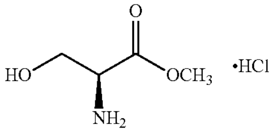 | L-Serine methyl ester hydrochloride 98% | $C_4H_9NO_3$•HCl |
| S5000 | 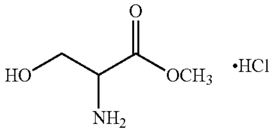 | DL-Serine methyl ester hydrochloride | $C_4H_9NO_3$•HCl |
| 223131 | 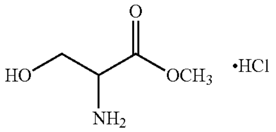 | DL-Serene methyl ester hydrochloride 98% | $C_4H_9NO_3$•HCl |
| CDS013925 | 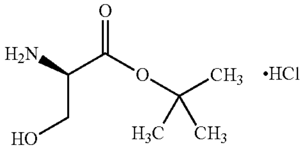 | H-Ser-OtBu hydrochloride Aldrich$^{CPR}$ | $C_7H_{15}ClNO_3$ |
| CDS015361 | 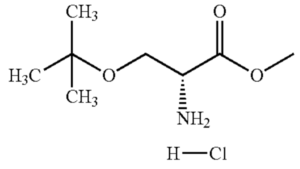 | hydrochloride Aldrich$^{CPR}$ | $C_8H_{18}ClNO_3$ |
| CDS004729 | 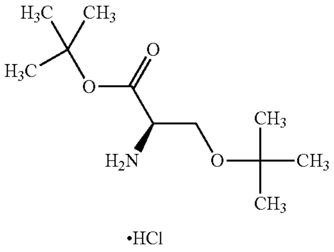 | H-D-Ser(tBu)-OtBu hydrochloride Aldrich$^{CPR}$ | $C_{11}H_{24}ClNO_3$ |
| 93470 | 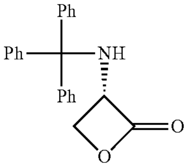 [SMILES: O=C1OC[C@@H]1NC(c1ccccc1)(c1ccccc1)c1ccccc1] | N-Trityl-L-serine lactone 98.0% (sum of enantiomers, TLC) | $C_{22}H_{19}NO_2$ |

-continued

| SERINE DERIVATIVES | | | |
|---|---|---|---|
| Product # | Image | Description | Molecular Formula |
| 411345 | 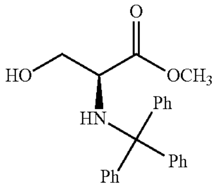 [SMILES: COC(=O)[C@H](CO)NC(c1ccccc1)(c1ccccc1)c1ccccc1] | N-Trityl-L-serine methyl ester 99% | $C_{23}H_{23}NO_3$ |
| 533122 | 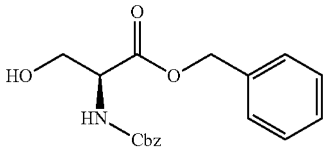 [SMILES: O=C(N[C@@H](CO)C(=O)OCc1ccccc1)OCc1ccccc1] | NZL-Serine benzyl ester 97% | $C_{18}H_{19}NO_5$ |
| 472964 | 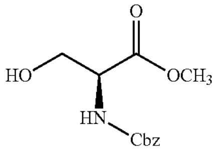 [SMILES: COC(=O)[C@H](CO)NC(=O)OCc1ccccc1] | NZ-D-serine methyl ester | $C_{12}H_{15}NO_5$ |
| 469165 | 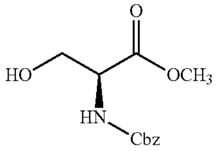 [SMILES: COC(=O)[C@H](CO)NC(=O)OCc1ccccc1] | N-Z-L-serine methyl ester 95% | $C_{12}H_{15}NO_5$ |
| 860700 | 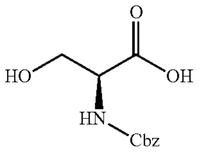 [SMILES: O=C(N[C@@H](CO)C(=O)O)OCc1ccccc1] | Z-Ser-OH ≥99% | $C_{11}H_{13}NO_5$ |
| C9004 | 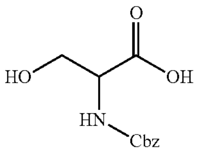 [SMILES: O=C(NC(CO)C(=O)O)OCc1ccccc1] | Z-DL-Ser-OH 99% | $C_{11}H_{13}NO_5$ |
| 96028 | 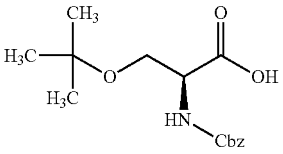 | Z-Ser(tBu)-OH ≥98.0% (TLC) | $C_{15}H_{21}NO_5$ |

See more at: http:/www.sigmaaldrich.com/chemistry/chemistry-products.html?TablePage=16248199#sthash.eqnGflUg.dpuf

TABLE 3

| Copper Compounds Subject to Reregistration. | | | | |
|---|---|---|---|---|
| Case | Chemical Name | EPA PC Code | C.A.S. Number | Registrants |
| Copper Sulfates #0636 | Basic Copper Sulfate | 008101 | 1344-73-6 | CSTF |
| | Copper Sulfate Pentahydrate | 024001 | 7758-99-8 | |
| | Copper sulfate monohydrate | 024402 | 1332-14-5 | Cancelled |
| | Copper sulfate Anhydrous | 024408 | 7758-98-7 | |

TABLE 3-continued

Copper Compounds Subject to Reregistration.

| Case | Chemical Name | EPA PC Code | C.A.S. Number | Registrants |
|---|---|---|---|---|
| Group II Copper Compounds #0649 | Copper Chloride | 008001 | 1332-40-7 | CSTF |
| | Copper Ammonium Carbonate | 022703 | 33113-08-5 | |
| | Basic Copper Carbonate | 022901 | 1184-64-1 | |
| | Copper Hydroxide | 023401 | 20427-59-2 | CSTF |
| | Copper Oxychloride | 023501 | 1332-65-6 | |
| | Copper Oxychloride Sulfate | 023503 | 8012-69-9 | |
| | Copper Ammonia Complex | 022702 | 16828-95-8 | |
| | Chelates of Copper Copper Gluconate | 023305 | 814-91-5 | CSTF |
| | Copper chloride dihydrate | 023701 | 10125-13-0 | Cancelled |
| | Copper Nitrate | 076102 | 3251-23-8 | |
| | Copper Oxalate | 023305 | 814-91-5 | |
| | Chelates of copper citrate | 044005 | 10402-15-0 | |
| Copper and Oxides #4025 | Cuprous Oxide Antimicrobial Uses Only | 025601 | 1317-39-1 | CRTF |
| | Copper (metal) | 022501 | 7440-50-8 | CRTF |
| | Cupric Oxide | 042401 | 1317-38-0 | |
| Copper Salts #4026 | Copper Salts of Fatty and Rosin Acids | 023104 | 9007-39-0 | CSTF |
| | Copper Ethylenediamine | 024407 | 13426-91-0 | Applied Biochemists |
| | Copper Triethanolamine Complex | 024403 | 82027-59-6 | |
| | Copper 2-ethylhexanoate (hexanoic acid) | 041201 | 22221-10-9 | Cancelled |
| | Copper etidronic acid complex | 024404 | 50376-91-5 | |
| | Copper dehydroabietyl ammonium 2-ethylhexanoate | 041202 | 53404-24-3 | |
| | Copper ethylenediaminetetraacetate (EDTA) | 039105 | 12276-01-6 | Unsupported |
| | Copper linoleate | 023303 | 7721-15-5 | Cancelled |
| | Copper oleate | 023304 | 10402-16-1 | |
| | Copper salts of the Acids of Tall Oil | 023103 | 61789-22-8 | |
| | Cupric ferric subsulfate complex Antimicrobial Uses Only | 042402 | 12168-20-6 | |
| | Copper Naphthenate | 023102 | 1338-02-9 | CRTF |
| | Copper 8-quinolinolate | 024002 | 10380-28-6 | |
| Other Copper Compounds | Copper Octanoate | 023306 | 20543-04-8 | CSTF |
| | Copper Ethanolamine Complex | 024409 | 14215-52-2 | Applied Biochemists |

What is claimed is:

1. A method of reducing population of microbe on an object, the method comprising: applying to the object a biofilm reducing agent, or a metal antimicrobial agent and a biofilm reducing agent, in amount and for time sufficient to reduce the microbial population, wherein the microbial population comprises *Xanthomonas citri* subsp. *citri* and the biofilm reducing agent comprises D-leucine, D-Serine, or 3-idolylacetonitrile.

2. The method of claim 1, wherein the metal antimicrobial agent comprises copper or silver; and optionally further comprises carrier and solvent.

3. The method of claim 2, wherein the metal antimicrobial agent comprises copper sulfate.

4. The method of claim 1, wherein applying comprises applying the biofilm reducing agent, or the metal antimicrobial agent and the biofilm reducing agent, to a *citrus* tree.

5. The method of claim 1, wherein applying comprises applying the biofilm reducing agent, or the metal antimicrobial agent and the biofilm reducing agent, to *citrus* fruit.

6. The method of claim 5, wherein the *citrus* fruit is on a *citrus* tree.

7. The method of claim 5, wherein the *citrus* fruit is off a *citrus* tree.

8. The method of claim 1, wherein applying comprises applying the biofilm reducing agent, or the metal antimicrobial agent and the biofilm reducing agent, to equipment used in a *citrus* orchard.

9. The method of claim 1, wherein applying comprises applying the biofilm reducing agent, or the metal antimicrobial agent and the biofilm reducing agent, to equipment used for transport or processing *citrus* fruit.

10. The method of claim 1, wherein applying the biofilm reducing agent, or the metal antimicrobial agent and the biofilm reducing agent, comprises injection into a trunk of a tree, administration to bark of a tree, administration to soil proximate to a tree, or irrigation of a tree.

11. The method of claim 1, wherein the metal antimicrobial agent and biofilm reducing agent are in an antimicrobial composition.

12. The method of claim 11, wherein the composition further comprises surfactant and a solvent.

13. A method of treating *citrus* canker comprising: applying to *citrus* tree a biofilm reducing agent, or a metal antimicrobial agent and a biofilm reducing agent, and optionally a surfactant, and alcohol, in amount and for time sufficient to treat *citrus* canker, wherein the biofilm reducing agent comprises D-leucine, D-Serine, or 3-indolylacetonitrile.

* * * * *